(12) United States Patent
Pollack

(10) Patent No.: US 10,254,299 B2
(45) Date of Patent: Apr. 9, 2019

(54) MULTIPLE SLOT PLACE AND PICK CARRIER

(71) Applicant: Benjamin S. Pollack, Budd Lake, NJ (US)

(72) Inventor: Benjamin S. Pollack, Budd Lake, NJ (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 78 days.

(21) Appl. No.: 14/434,570

(22) PCT Filed: Oct. 11, 2013

(86) PCT No.: PCT/US2013/064620
§ 371 (c)(1),
(2) Date: Apr. 9, 2015

(87) PCT Pub. No.: WO2014/059322
PCT Pub. Date: Apr. 17, 2014

(65) Prior Publication Data
US 2015/0276774 A1 Oct. 1, 2015

Related U.S. Application Data

(60) Provisional application No. 61/712,670, filed on Oct. 11, 2012.

(51) Int. Cl.
| | |
|---|---|
| *G01N 35/02* | (2006.01) |
| *G01N 35/00* | (2006.01) |
| *G01N 35/04* | (2006.01) |
| *B65G 17/32* | (2006.01) |
| *B65G 47/90* | (2006.01) |

(52) U.S. Cl.
CPC ............ *G01N 35/02* (2013.01); *B65G 17/32* (2013.01); *B65G 47/90* (2013.01);
(Continued)

(58) Field of Classification Search
CPC ............... G01N 35/04; G01N 35/0092; G01N 35/0099; G01N 2035/0406;
(Continued)

(56) References Cited

U.S. PATENT DOCUMENTS

| | | | | |
|---|---|---|---|---|
| 5,557,881 A | * | 9/1996 | Bouldin ............... | A01C 11/025 111/105 |
| 6,204,764 B1 | * | 3/2001 | Maloney ................ | G06K 17/00 235/375 |

(Continued)

FOREIGN PATENT DOCUMENTS

| | | |
|---|---|---|
| EP | 0 931 259 B1 | 11/2006 |
| WO | 2001/086410 A1 | 11/2001 |

OTHER PUBLICATIONS

PCT International Search Report and Written Opinion dated Mar. 11, 2014 (9 Pages).

*Primary Examiner* — Saul Rodriguez
*Assistant Examiner* — Ronald P Jarrett

(57) ABSTRACT

An automation system for use with in-vitro diagnostics includes a plurality of fluid containers configured to hold one or more fluids. The system includes a plurality of carriers having a plurality of slots configured to hold one of the plurality of fluid containers. The system also includes a place and pick device configured to place the plurality of fluid containers into the plurality of slots and remove the plurality of fluid containers from the plurality of slots. The system further includes a controller configured to control the place and pick device to place a first fluid container into an empty slot of a carrier of the plurality of carriers while a second fluid container is in an occupied slot and control the place and pick device to subsequently remove the second fluid container from the occupied slot of the carrier.

16 Claims, 21 Drawing Sheets

(52) U.S. Cl.
CPC ..... *G01N 35/0092* (2013.01); *G01N 35/0099* (2013.01); *G01N 35/04* (2013.01); *G01N 2035/0406* (2013.01); *G01N 2035/047* (2013.01); *G01N 2035/0467* (2013.01)

(58) Field of Classification Search
CPC ... G01N 2035/0415; G01N 2035/0467; G01N 2035/047
USPC .............................................. 422/63, 65, 624
See application file for complete search history.

(56) References Cited

U.S. PATENT DOCUMENTS

| | | | |
|---|---|---|---|
| 6,343,690 B1 * | 2/2002 | Britton | B65G 17/002 198/803.6 |
| 6,429,016 B1 * | 8/2002 | McNeil | G01N 35/0099 414/222.02 |
| 7,141,213 B1 * | 11/2006 | Pang | G01N 35/0095 422/65 |
| 7,964,413 B2 | 6/2011 | Macioszek et al. | |
| 8,272,827 B2 | 9/2012 | Bufano et al. | |
| 2005/0004703 A1 | 1/2005 | Christie et al. | |
| 2008/0209709 A1 * | 9/2008 | Mayer | B01D 61/18 29/426.5 |
| 2011/0158850 A1 * | 6/2011 | Pedrazzini | B01L 9/02 422/65 |

* cited by examiner

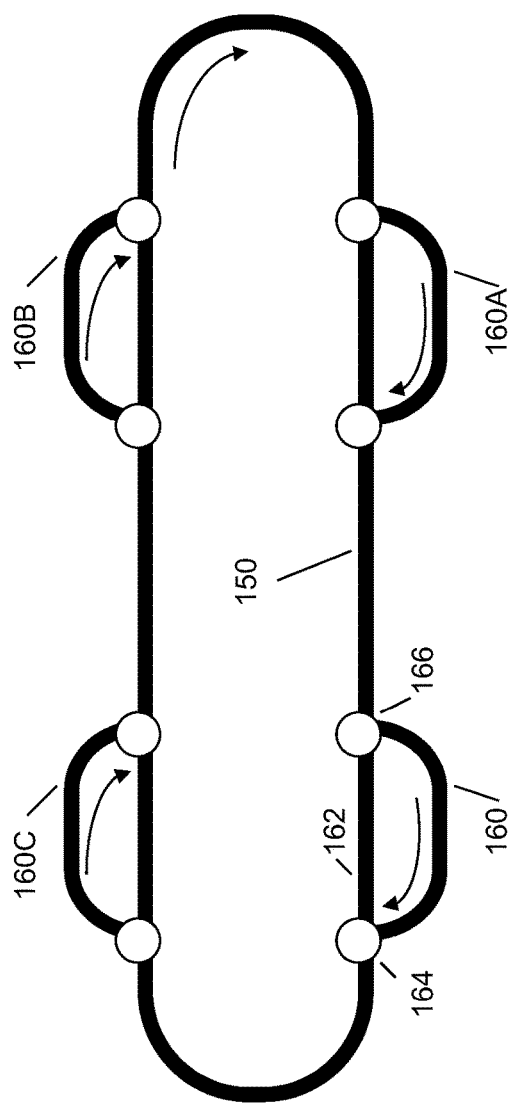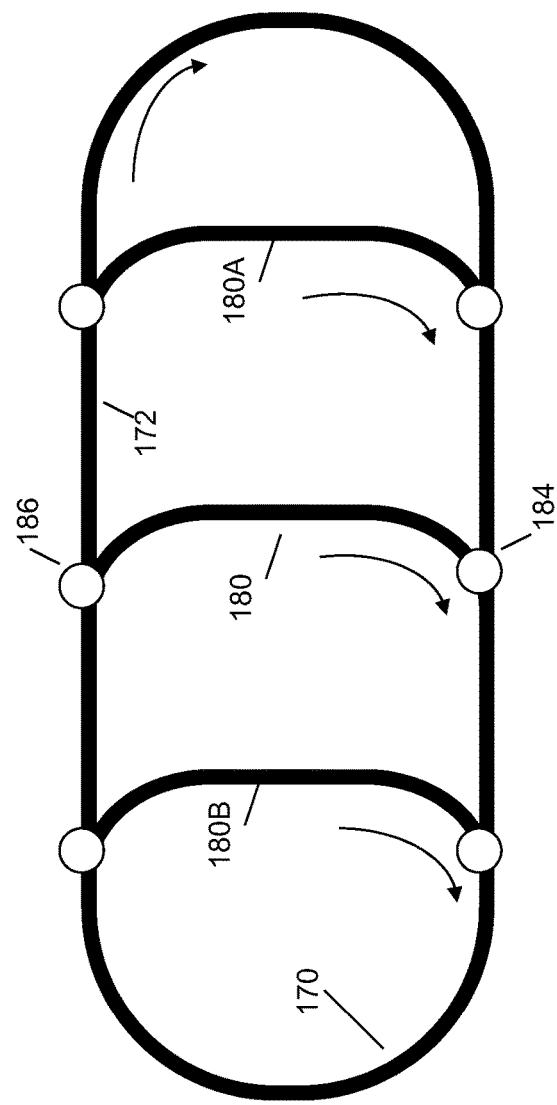

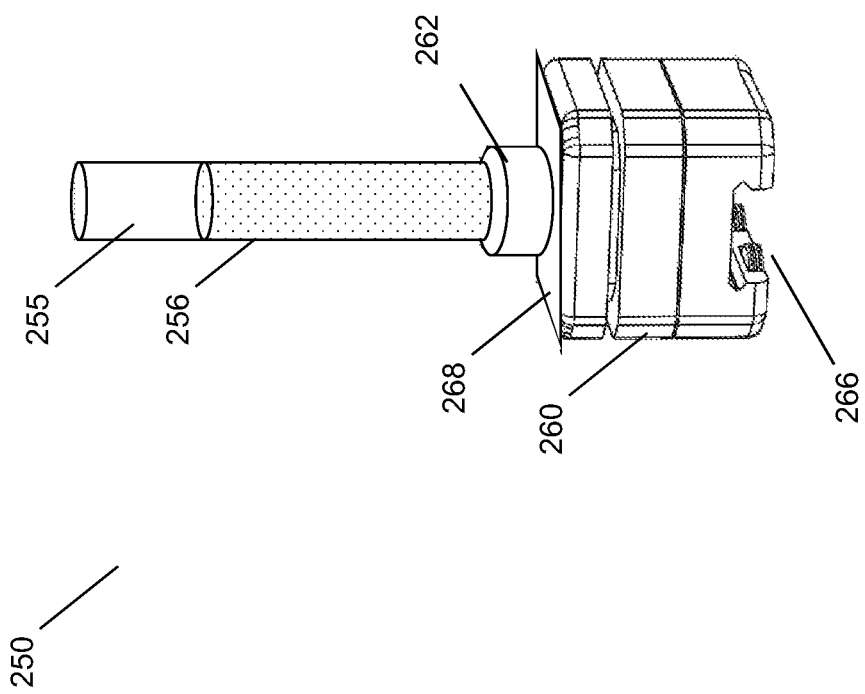

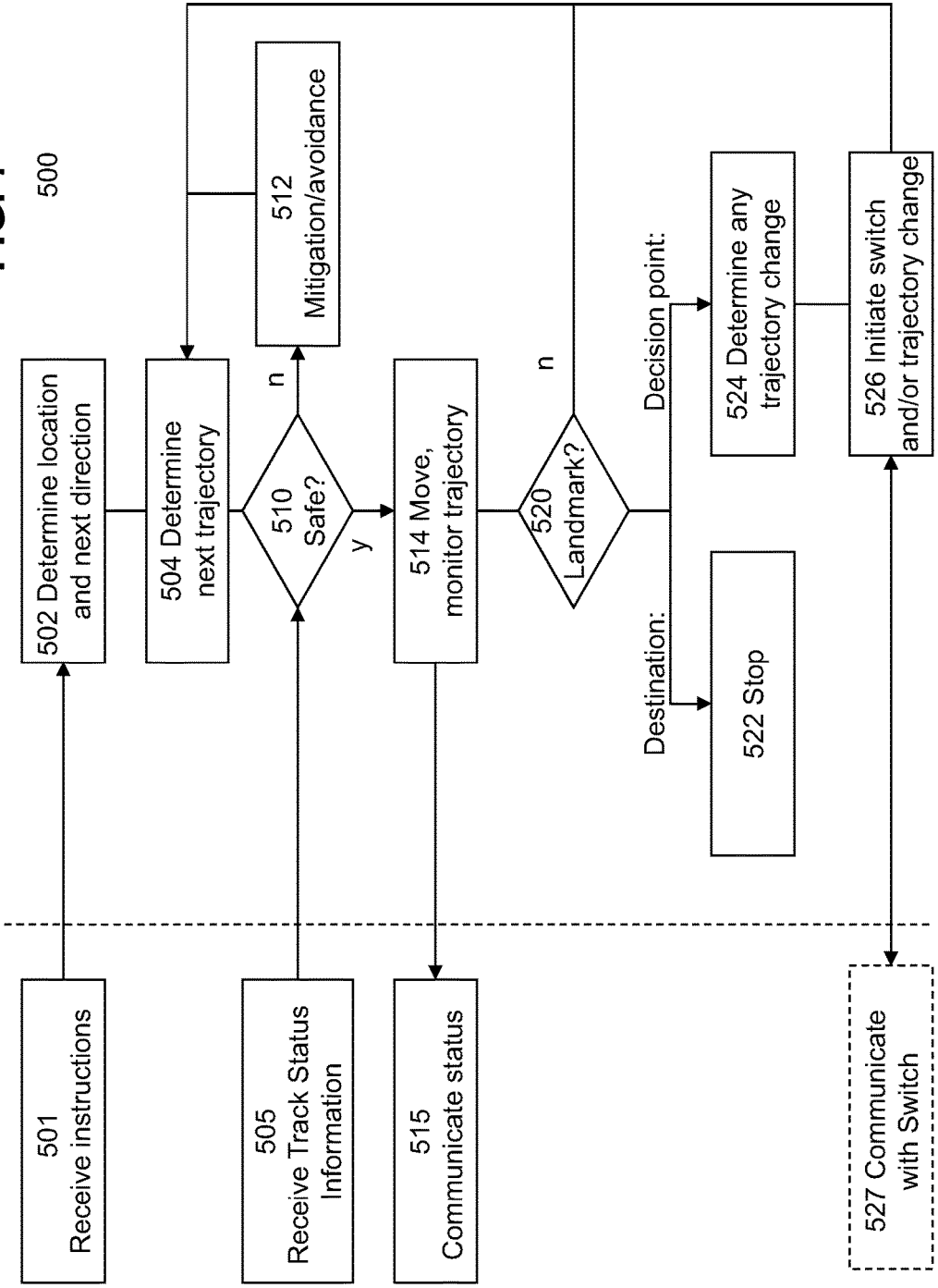

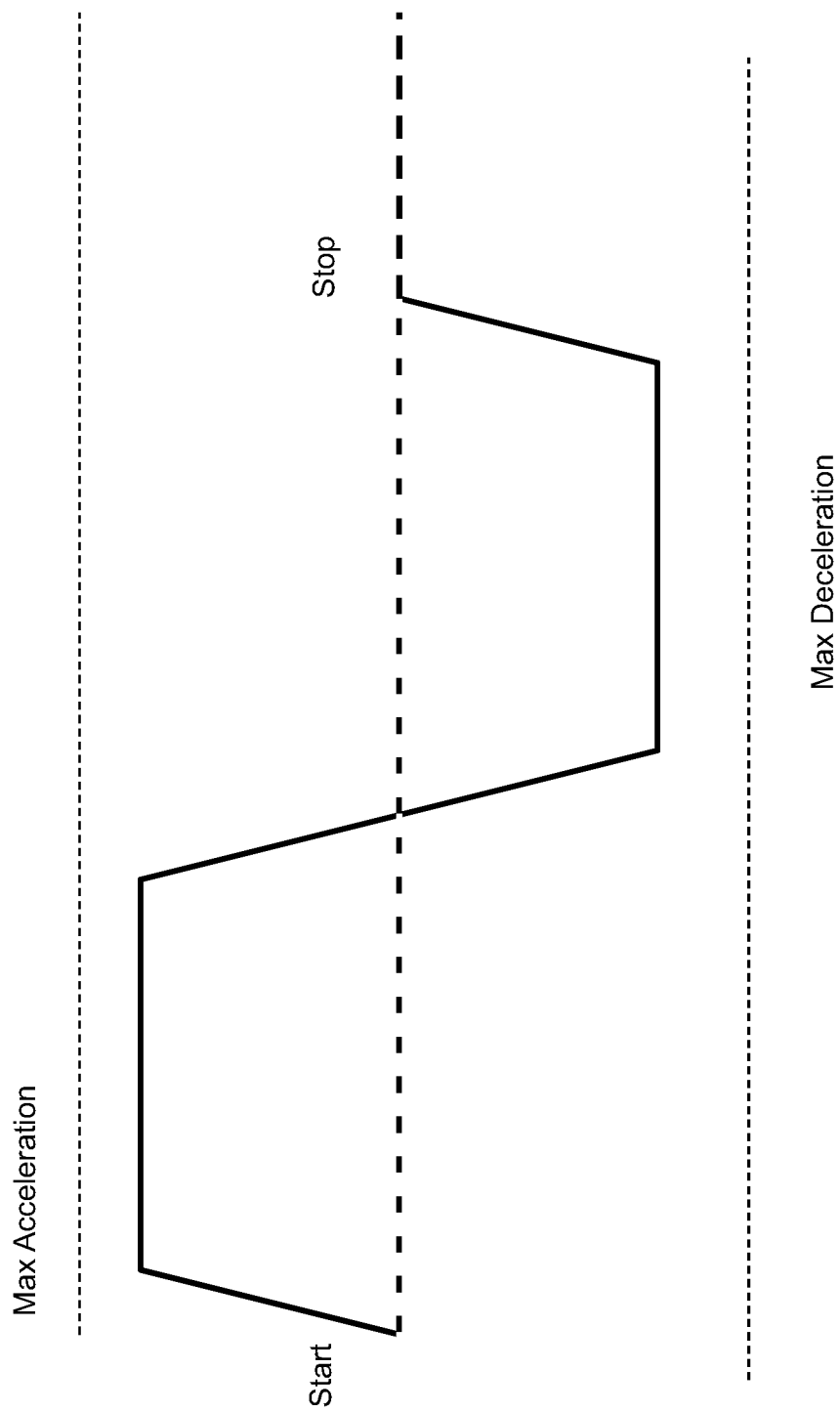

MULTIPLE SLOT PLACE AND PICK CARRIER

This application claims priority to U.S. provisional application Ser. No. 61/712,670 filed Oct. 11, 2012, which is incorporated herein by reference in its entirety.

TECHNOLOGY FIELD

The present invention relates in general to an automation system for use in a laboratory environment and, more particularly, to systems and methods for transporting patient samples for in-vitro diagnostics in a clinical analyzer.

BACKGROUND

In-vitro diagnostics (IVD) allows labs to assist in the diagnosis of disease based on assays performed on patient fluid samples. IVD includes various types of analytical tests and assays related to patient diagnosis and therapy that can be performed by analysis of a liquid sample taken from a patient's bodily fluids, or abscesses. These assays are typically conducted with automated clinical chemistry analyzers (analyzers) onto which fluid containers, such as tubes or vials containing patient samples have been loaded. The analyzer extracts a liquid sample from the vial and combines the sample with various reagents in special reaction cuvettes or tubes (referred to generally as reaction vessels). In some conventional systems, a modular approach is used for analyzers. A lab automation system can shuttle samples between one sample processing module (module) and another module. Modules may include one or more stations, including sample handling stations and testing stations (e.g., a unit that can specialize in certain types of assays or can otherwise provide testing services to the larger analyzer), which may include immunoassay (IA) and clinical chemistry (CC) stations. Some traditional IVD automation track systems comprise systems that are designed to transport samples from one fully independent module to another standalone module. This allows different types of tests to be specialized in two different stations or allows two redundant stations to be linked to increase the volume of sample throughput available.

In some conventional systems, individual carrier mechanisms (carriers), sometimes called pucks, or racks of containers are shuttled between different stations. Samples may be stored in sample containers, such as test tubes, that are placed into a carrier by an operator or a place and pick device for transport between stations in an analyzer along the track. The place and pick device is used to unload individual test tubes from the carriers to the tube storage area and load individual test tubes from a tube storage area onto the carriers. A discrete "place" operation is performed when the place and pick device loads (places) a tube from storage onto the carrier. A discrete "pick" operation is performed when the place and pick device removes (picks) a tube from a carrier and transports the tube to storage.

The place operation and pick operation may be combined into a single combined place and pick operation. That is, the place and pick device may perform a combined place and pick operation by placing a tube onto the carrier and then picking another tube from an adjacent carrier before transporting the picked tube to storage and returning to place a retrieved tube from storage onto the adjacent carrier. The adjacent carrier must, however, wait until the place and pick device returns from storage with the retrieved tube from storage before it can move toward its next destination. For this reason, some conventional systems experience sample handling queues at place and pick devices. Accordingly, one or more carriers must wait in the sample handling queue during the time required for the place and pick device to transport a picked tube from a carrier to storage and place a retrieved tube from storage onto a carrier.

SUMMARY

Embodiments of the present invention include an automation system for use with in-vitro diagnostics that includes a track configured to provide one or more paths and a plurality of carriers configured to travel along the track. Each carrier includes a plurality of slots. Each slot is configured to hold one of a plurality of fluid containers. The system also includes a place and pick device configured to place the plurality of fluid containers into the plurality of slots and remove the plurality of fluid containers from the plurality of slots. The system further includes and a controller configured to control the place and pick device to: (i) control the place and pick device to place a first fluid container into an empty slot of a carrier of the plurality of carriers while a second fluid container is in an occupied slot; (ii) control the place and pick device to subsequently remove the second fluid container from the occupied slot of the carrier; and (iii) maintain the empty slot on the carrier prior to the first fluid container being placed into the empty slot.

According to one embodiment of the invention, the system further includes a storage area accessible to the place and pick device and configured to hold the plurality of fluid containers. The controller is further configured to control the place and pick device to: (i) retrieve the first fluid container from the storage area prior to placing the first fluid container into the empty slot of the carrier; and (ii) store the second fluid container at the storage area after removing the second fluid container from the carrier.

According to another embodiment of the invention, the system further includes one or more sensors configured to sense at least one of: (i) which of the plurality of slots of each carrier is empty; and (ii) which of the plurality of slots of each carrier is occupied.

According to an aspect of an embodiment, at least one carrier of the plurality of carriers includes the one or more sensors. According to another aspect of an embodiment, the one or more sensors are configured to observe at least one carrier of the plurality of carriers.

According to one embodiment of the invention, the controller is configured to direct at least one of the plurality of carriers to: (i) a first carrier location for having the first fluid container placed into the empty slot; and (ii) a second carrier location for having the second fluid container subsequently removed from the occupied slot.

According to another embodiment of the invention, at least one carrier of the plurality of carriers comprises an onboard processor.

According to an aspect of an embodiment, the at least one carrier further includes a transceiver configured to communicate with the onboard processor and the controller. According to another aspect of an embodiment, the plurality of slots further includes at least three slots.

According to one aspect, the system further includes a plurality of electromagnetic coils in at least one of the track and the plurality of carriers and a plurality of magnets in at least one of the other of the track and the plurality of carriers. The plurality of electromagnetic coils and the plurality of magnets are configured to propel the plurality of carriers along the track.

Embodiments of the present invention include a carrier for transporting fluids in an in-vitro diagnostics environment that includes a carrier body and at least two slots. Each slot is configured to hold one of a plurality of fluid containers. The carrier also includes one or more sensors configured to sense at least one of: (i) which of the at least two slots of each carrier is empty; and (ii) which of the at least two slots of each carrier is occupied. Each fluid container is configured to hold one or more fluids.

According to one embodiment of the invention, the carrier further includes an onboard processor. In an aspect of the embodiment, the onboard processor is configured to direct the carrier to: (i) a first carrier location for having a first fluid container placed into an empty slot; and (ii) a second carrier location for having a second fluid container subsequently removed from an occupied slot.

According to another embodiment of the invention, the carrier further includes a communications system configured to receive routing instructions, including: (i) a first carrier location for having a first fluid container placed into an empty slot; and (ii) a second carrier location for having a second fluid container subsequently removed from an occupied slot.

According to one embodiment of the invention, the at least two slots further include at least three slots. According to another embodiment of the invention, the carrier is configured to be propelled along a track via magnetic forces.

Embodiments of the present invention include a method for operating an in-vitro diagnostics system that includes moving a plurality of carriers having a plurality of slots and configured to travel along a track. The method also includes directing a carrier of the plurality of carriers to a location along the track and placing a first fluid container, using a place and pick device, into an empty slot of the carrier at the location while a second fluid container is in an occupied slot. The method further includes removing the second fluid container, using the place and pick device, from the occupied slot of the carrier subsequent to placing the first fluid container into the empty slot.

According to one embodiment of the invention, the method further includes directing the carrier to a second location along the track prior to removing the second fluid container from the occupied slot of the carrier.

According to an aspect of an embodiment, the method further includes retrieving the first fluid container from a storage area prior to placing the first fluid container into the empty slot of the carrier and storing the second fluid container at the storage area after removing the second fluid container from the carrier.

According to one embodiment of the invention, the method further includes sensing at least one of: (i) which of the plurality of slots of each carrier is empty; and (ii) which of the plurality of slots of each carrier is occupied.

BRIEF DESCRIPTION OF THE DRAWINGS

The foregoing and other aspects of the present invention are best understood from the following detailed description when read in connection with the accompanying drawings. For the purpose of illustrating the invention, there is shown in the drawings embodiments that are presently preferred, it being understood, however, that the invention is not limited to the specific instrumentalities disclosed. Included in the drawings are the following Figures:

FIG. 2A and FIG. 2B are diagrammatic views of track geometries that can be used with the automation system embodiments disclosed herein;

FIG. 4A is a perspective view of an exemplary carrier that can be used with the embodiments disclosed herein;

FIG. 7 is a flow diagram showing the operation of the navigation of sample carriers in certain embodiments;

FIG. 8 is an exemplary acceleration profile used by sample carriers in certain embodiments;

DETAILED DESCRIPTION OF ILLUSTRATIVE EMBODIMENTS

Figure 1:
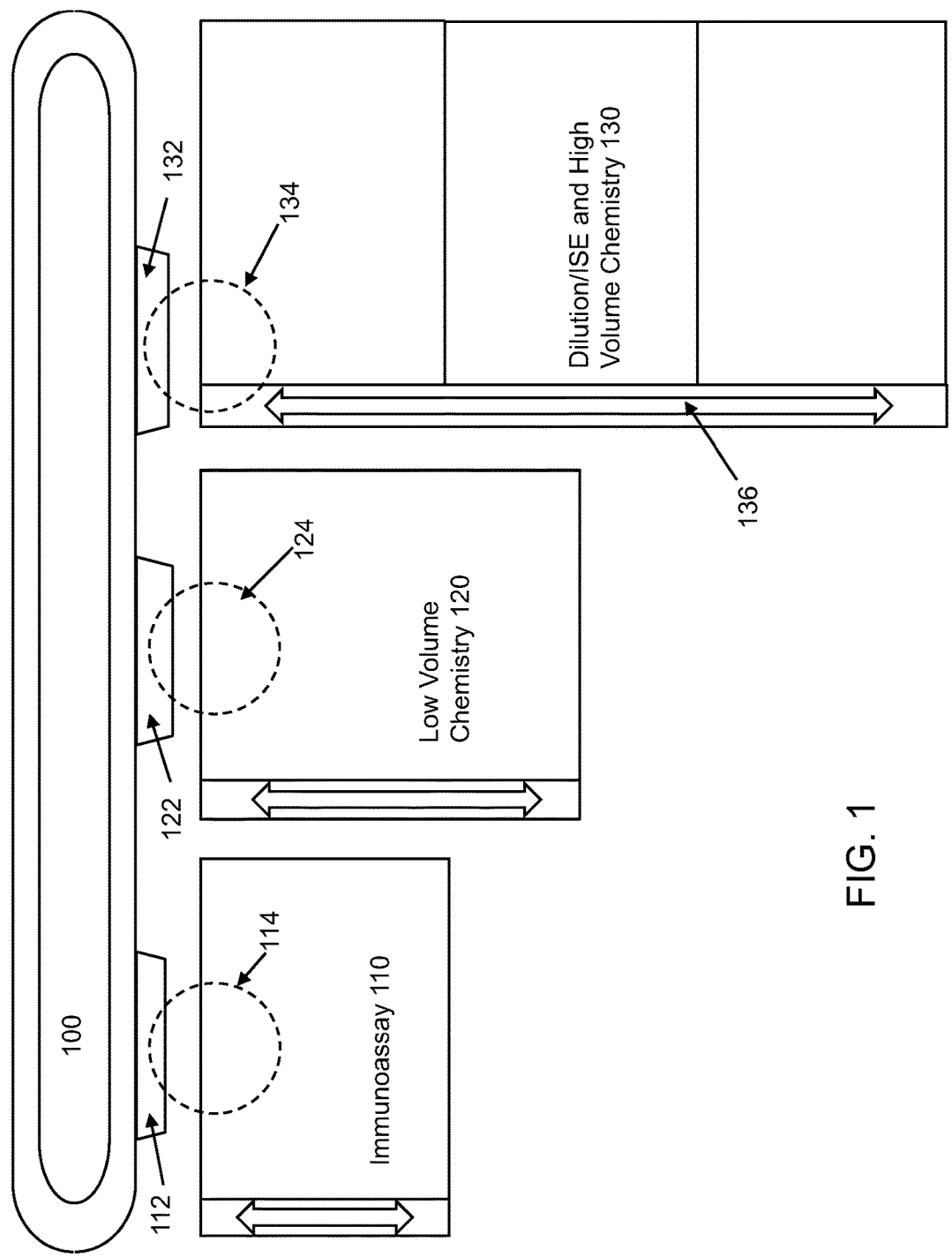
FIG. 1 is a top view of an exemplary clinical analyzer geometry that can be improved by use of the automation system embodiments disclosed.

Terms and Concepts Associated with Some Embodiments

Analyzer: Automated clinical analyzers ("analyzers") include clinical chemistry analyzers, automated immunoassay analyzers, or any other type of in vitro diagnostics (IVD) testing analyzers. Generally, an analyzer performs a series of automated IVD tests on a plurality of patient samples. Patient samples may be loaded into an analyzer (manually or via an automation system), which can then perform one or more immunoassays, chemistry tests, or other observable tests on each sample. The term analyzer may refer to, but is not limited to, an analyzer that is configured as a modular analytical system. A modular analytical system includes an integrated and extendable system comprising any combinations of a plurality of modules (which can include the same type of module or different types of modules) interconnected in a linear or other geometric configuration by an automation surface, such as an automation track. In some embodiments, the automation track may be configured as an integral conveyance system on which independent carriers are used to move patient samples and other types of material between the modules. Generally, at least one module in a modular analytical system is an analyzer module. Modules may be specialized or made redundant to allow higher throughput of analytical tasks on patient samples.

Analyzer module: An analyzer module is a module within a modular analyzer that is configured to perform IVD tests, such as immunoassays, chemistry tests, or other observable tests on patient samples. Typically, an analyzer module extracts a liquid sample from a sample vessel and combines the sample with reagents in reaction cuvettes or tubes (referred to generally as reaction vessels). Tests available in an analyzer module may include, but are not limited to, a subset of electrolyte, renal or liver function, metabolic, cardiac, mineral, blood disorder, drug, immunoassay, or other tests. In some systems, analyzer modules may be specialized or made redundant to allow higher throughput. The functions of an analyzer module may also be performed by standalone analyzers that do not utilize a modular approach.

Carrier: A carrier is a transportation unit that can be used to move sample vessels (and, by extension, fluid samples) or other items in an automation system. In some embodiments, carriers may be simple, like traditional automation pucks (e.g., passive devices comprising a holder for engaging a tube or item, a friction surface to allow an external conveyor belt in the automation track to provide motive force, and a plurality of sides that allow the puck to be guided by walls or rails in the automation track to allow the track to route a puck to its destination). In some embodiments, carriers may include active components, such as processors, motion systems, guidance systems, sensors, and the like. In some embodiments, carriers can include onboard intelligence that allows carriers to be self-guided between points in an automation system. In some embodiments, carriers can include onboard components that provide motive forces while, in others, motive forces may be provided by an automation surface, such as a track. In some embodiments, carriers move along automation tracks that restrict motion to a single direction (e.g., fore and aft) between decision points. Carriers may be specialized to a given payload in an IVD environment, such as having a tube holder to engage and carry a sample tube, or may include mounting surfaces suitable to carry different items around an automation system. Carriers can be configured to include one or more slots (e.g., a carrier may hold one or a plurality of sample vessels).

Central controller or processor: A central controller/processor (which may sometimes be referred to as a central scheduler) is a processor that is part of the automation system, separate from any processors onboard carriers. A central controller can facilitate traffic direction, scheduling, and task management for carriers. In some embodiments, a central controller can communicate with subsystems in the automation system and wirelessly communicate with carriers. This may also include sending trajectory or navigational information or instructions to carriers and determining which carriers should go where and when. In some embodiments, local processors may be responsible for managing carriers on local track sections, such as managing local queues. These local processors may act as local equivalents to central controllers.

Decision point: Decision points are points on an automation track where different navigational or trajectory decisions may be made for different carriers. A common example includes a fork in a track. One carrier may proceed without turning, while another may slow down and turn. Decision points may include stopping points at instruments, where some carriers may stop, while others may proceed. In some embodiments, deceleration zones ahead of turns may act as decision points, allowing carriers that will be turning to slow down to limit lateral forces, while others may proceed if not turning or if the motion profile for that carrier does not require slowing down. The decisions made at decision points can be made by processors onboard carriers, processors local to the track section, a central processor, or any combination thereof, depending on the embodiment.

Independent carrier: In some embodiments, carriers may be characterized as independently controlled carriers. Independently controlled carriers, are carriers with independently controlled trajectories. In some embodiments, independent carriers may be operating at the same time, on the same track, with carriers carrying one or a plurality of combinations of payloads that differ by size, weight, form factor, and/or content. The trajectories of each independently controlled carrier may be limited by a motion profile that includes maximum jerk, acceleration, direction, and/or speed for the carrier while moving in the automation system. The motion profile can limit or define the trajectory for each carrier independently. In some embodiments, a motion profile can be different for different sections of the automation system (e.g., in straight track sections vs. around curves to account for the added lateral forces while turning), for different carrier states (e.g., an empty carrier may have a different motion profile from a carrier transporting a sample or from a carrier transporting a reagent or other item), and/or for different carriers. In some embodiments, carriers can include onboard propulsion components that allow individual carriers to independently operate responsive to a motion profile or trajectory or destination instructions intended for each separate carrier.

Intelligent carrier/semi-autonomous carriers: In some embodiments, carriers may be characterized as intelligent carriers. An intelligent carrier is a carrier with onboard circuits that participates in motion, routing, or trajectory decisions. An intelligent carrier can include digital processors that execute software instructions to proceed along an automation surface responsive to the instructions or onboard analog circuits that respond to motion input (e.g., line follower circuits). Instructions may include instructions characterizing motion profiles, traffic, or trajectory rules. Some intelligent carriers may also include onboard sensors to assist onboard processors to route the carrier or make decisions responsive to the carrier's environment. Some intelligent carriers may include onboard components, such as motors or magnets, which allow the carrier to move responsive to control of an onboard processor.

In vitro diagnostics (IVD): In vitro diagnostics (IVD) are tests that can detect diseases, conditions, infections, metabolic markers, or quantify various constituents of bodily materials/fluids. These tests are performed in laboratory, hospital, physician office, or other health professional settings, outside the body of a patient. IVD testing generally utilizes medical devices intended to perform diagnoses from assays in a test tube or other sample vessel or, more generally, in a controlled environment outside a living organism. IVD includes testing and diagnosis of disease or quantifying various constituents of bodily materials/fluids based on assays performed on patient fluid samples. IVD includes various types of analytical tests and assays related to patient diagnosis and therapy that can be performed by analysis of a liquid sample taken from a patient's bodily fluids, or abscesses. These assays are typically conducted with analyzers into which tubes or vials containing patient samples have been loaded. IVD can refer to any subset of the IVD functionality described herein.

Landmarks: In embodiments where carriers include onboard sensors, optical or other marks in track surfaces or locations viewable/sensible from track surfaces can act as landmarks. Landmarks can convey geographic information to carriers, such as a current location, upcoming stopping location, decision point, turn, acceleration/deceleration points, and the like.

Lab automation system: Lab automation systems include any systems that can automatically (e.g., at the request of an operator or software) shuttle sample vessels or other items within a laboratory environment. With respect to analyzers, an automation system may automatically move vessels or other items to, from, amongst, or between stations in an analyzer. These stations may include, but are not limited to, modular testing stations (e.g., a unit that can specialize in certain types of assays or can otherwise provide testing services to the larger analyzer), sample handling stations, storage stations, or work cells.

Module: A module performs specific task(s) or function(s) within a modular analytical system. Examples of modules may include: a pre-analytic module, which prepares a sample for analytic testing, (e.g., a decapper module, which removes a cap on top of a sample test tube); an analyzer module, which extracts a portion of a sample and performs tests or assays; a post-analytic module, which prepares a sample for storage after analytic testing (e.g., a recapper module, which reseals a sample test tube); or a sample handling module. The function of a sample handling module may include managing sample containers/vessels for the purposes of inventory management, sorting, moving them onto or off of an automation track (which may include an integral conveyance system, moving sample containers/vessels onto or off of a separate laboratory automation track, and moving sample containers/vessels into or out of trays, racks, carriers, pucks, and/or storage locations.

Payload: While exemplary carriers are described with respect to carrying patient samples, in some embodiments, carriers can be used to transport any other reasonable payload across an automation system. This may include fluids, fluid containers, reagents, waste, disposable items, parts, or any other suitable payloads.

Processor: A processor may refer to one or more processors and/or related software and processing circuits. This may include single or multicore processors, single or multiple processors, embedded systems, or distributed processing architectures, as appropriate, for implementing the recited processing function in each embodiment.

Pullouts, sidecars, offshoot paths: These terms may be used to refer to track sections that are off the main portion of a track system. Pullouts or sidecars may include chords, parallel tracks, or other suitable means for separating some carriers from a primary traffic pattern. Pullouts or sidecars may be configured to facilitate physical queues or allow certain carriers to stop or slow down without disrupting traffic on a main track section.

Samples: Samples refers to fluid or other samples taken from a patient (human or animal) and may include blood, urine, hematocrit, amniotic fluid, or any other fluid suitable for performing assays or tests upon. Samples may sometimes refer to calibration fluids or other fluids used to assist an analyzer in processing other patient samples.

STAT (short turnaround time) sample: Samples may have different priority assigned by a laboratory information system (LIS) or operator to assign STAT priority to samples that should take precedent over non-STAT samples in the analyzer. When used judiciously, this may allow certain samples to move through the testing process faster than other samples, allowing physicians or other practitioners to receive testing results quickly.

Station: A station includes a portion of a module that performs a specific task within a module. For example, the pipetting station associated with an analyzer module may be used to pipette sample fluid out of sample containers/vessels being carried by carriers on an integrated conveyance system or a laboratory automation system. Each module can include one or more stations that add functionality to a module.

Station/module: A station includes a portion of an analyzer that performs a specific task within an analyzer. For example, a capper/decapper station may remove and replace caps from sample vessels; a testing station can extract a portion of a sample and perform tests or assays; a sample handling station can manage sample vessels, moving them onto or off of an automation track, and moving sample vessels into or out of storage locations or trays. Stations may be modular, allowing stations to be added to a larger analyzer. Each module can include one or more stations that add functionality to an analyzer, which may be comprised of one or more modules. In some embodiments, modules may include portions of, or be separate from, an automation system that may link a plurality of modules and/or stations. Stations may include one or more instruments for performing a specific task (e.g., a pipette is an instrument that may be used at an immunoassay station to interact with samples on an automation track). Except where noted otherwise, the concepts of module and station may be referred to interchangeably.

Tubes/sample vessels/fluid containers: Samples may be carried in vessels, such as test tubes or other suitable vessels, to allow carriers to transport samples without contaminating the carrier surfaces.

Embodiments of the present invention include systems and methods that provide a more efficient lab automation system for moving sample carriers between various modular testing stations by utilizing multiple slot carriers configured to temporarily hold more than one sample, enabling a place and pick device to perform a combined place and pick operations may eliminate the time required for a sample carrier to wait in a sample queue while the place and pick device transports a picked sample from the sample carrier to a storage area and returns with a new sample from the storage area to be placed in the sample carrier. A combined place and pick operation includes having a single multiple slot carrier receive a sample from a place and pick carrier before having a resident sample picked or removed from the carrier by the place and pick carrier. Embodiments of the present invention include systems and methods that provide a lab automation system to perform place and pick operations more efficiently than a discrete place operation and a discrete pick operation using combined place and pick operations. Some embodiments of the present invention can reduce or eliminate sample handling queues experienced by carriers at place and pick devices, without the need for side cars, by utilizing combined place and pick operations.

Exemplary Automation System

An exemplary track geometry, for use in a transporting samples within an analyzer typical in prior art configurations, is shown in FIG. 1. As used herein, an analyzer can refer to any automated system for preparing or testing properties of patient samples in an automated manner. This track can include prior art friction tracks, which may introduce problems in designing a track system. However, certain embodiments of the present invention could also use a similar geometry without necessarily employing a friction track for motion. Track 100 can be a generally oval-shaped track that conveys samples in pucks or trays between various stations, such as sample preparation or analyzing/testing stations 110, 120, and 130. Track 100 could be a single direction track or, in some instances, a linear bidirectional track. In this exemplary set-up, each analyzer 110, 120, 130 is serviced by a respective sidecar 112, 122, 132. At the junction between the track 100 and each sidecar, a gate or switch can be placed that allows samples to be diverted to or from track 100 to the sidecar. The oval nature of track 100 can be used to circulate samples while they wait for access to each analyzer. For example, analyzer 110 may have a full queue in sidecar 112, such that new samples on track 100 cannot be diverted to sidecar 112 until analyzer 110 finishes handling a pending sample in sidecar 112 and inserts it back into the main traffic flow of track 100.

In some prior art systems, each sidecar can be serviced by a handling mechanism such as sample probe arms 114, 124, and 134. These robotic handling arms can aspirate sample material from samples in a sidecar via a probe needle, or can pick up a sample tube from the sidecar and transport it into the corresponding testing station. In this exemplary system, the available testing stations include an immunoassay station 110, a low-volume chemistry station 120, and an expandable dilution/ISE electrolyte and high-volume chemistry station (or stations) 130. Some advantages of this approach are that the track 100 can be part of a separate lab automation system that can be added onto otherwise self-contained stations, and the track 100 and stations 110, 120, and 130 can be independently upgraded, purchased, or serviced. Some stations, such as high-volume chemistry station 130, can include their own friction track 136 that operates independently of track 100. Friction track 136 can include a bidirectional friction track that allows samples to move between sub-modules of high-volume chemistry station 130. A drawback of this type of system is that the separate friction tracks operate independently and control of overall automation becomes more complicated. Furthermore, transitions between friction tracks 136 and 100 can be slow and cumbersome, particularly where there is no direct route between two friction tracks. In some systems, moving between tracks may require lifting and placing samples via a robot arm.

Prior art lab automation systems for analyzers generally treat individual analyzer/testing stations as generic destinations for a sample on the track. In some embodiments of the present invention, the lab automation system can be integrated within the individual testing stations, which can substantially reduce or eliminate the complexity of the individual testing stations and reduce the need for separate sample handling systems within each station. In some embodiments, by integrating the lab automation system into the stations, the system can begin to treat individual stations less as generic destinations and more as portions of a multi-route track onto which a sample can travel.

FIG. 2A shows one embodiment of a track system that can be adapted for use with the present invention. Track 150 is a rectangular/oval/circular track on which sample carriers move in a clockwise (or counterclockwise) direction. Track 150 may be unidirectional or bidirectional. Carriers can transport any suitable payload within an IVD environment, such as fluid samples, reagents, or waste. Fluids, such as patient samples can be placed in a container or vessel, such as a test tube, vial, cuvette, etc. that can be transported by a carrier. Carrier, as used herein, is a general term for pucks, trays, or the like for handling material in accordance with the disclosed embodiments. Carriers, and by extension payloads such as samples, can move on the main track 150 or be diverted via decision points such as 164 or 166. These decision points can be mechanical gates (as in the prior art) or other mechanisms suitable for allowing a sample to be diverted from the main track 150 to a sidecar, such as 160, 160A, 160B, 160C as described herein. By way of example, if a sample carrier is traversing the main path 150 and reaches decision point 166, it can be made to continue on the main track to segment 162 or it can be made to divert to sidecar 160. The systems and methods by which the decision can be made to divert the sample carrier at decision point 166 are described throughout.

FIG. 2B shows an alternative track layout that may be suitable for certain embodiments of the present invention. Track 170 is also a generally circular track with sample carriers moving clockwise (or counterclockwise). In this example, rather than having sidecars outside of the track, pullouts 180, 180A, and 180B are chords within the track. Similarly, when sample carriers reach decision points, they may be diverted off of the main path to a side path such as path 180. At decision point 186, a sample on the main track 170 can be made to continue on the main track or be diverted onto path 180. Once an analyzer station along handling path 180 is done processing the sample, the sample proceeds to decision point 184 where it may be placed back onto the main path 170.

Figure 3:
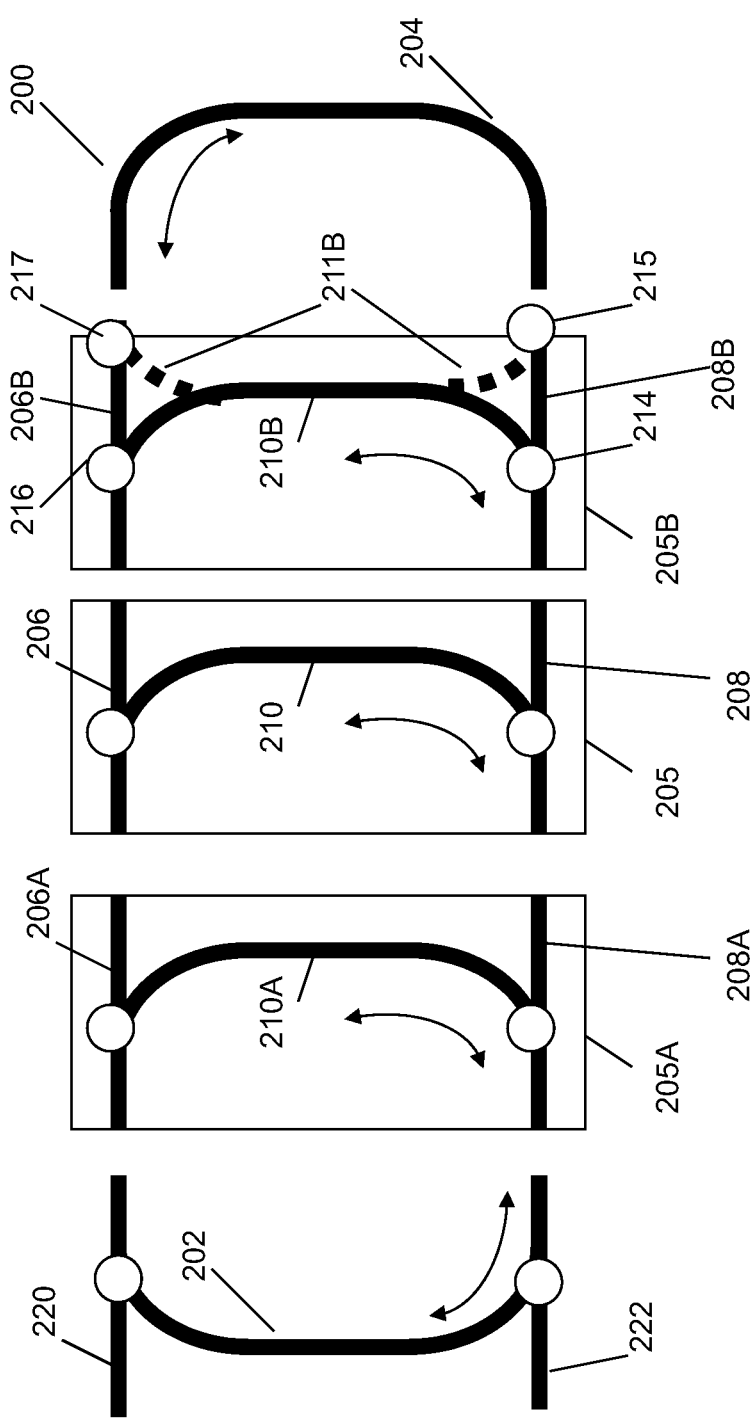
FIG. 3 is a diagrammatic view of an exemplary modular track configuration that can be used with the embodiments disclosed herein.

FIG. 3 shows a modular approach to the automation system track that can be used for certain embodiments of the present invention. In this example, the tracks may be integrated into individual analyzer stations, such that the track can be used as part of the internal motion or sample handling system of individual lab stations. In the prior art, it is common to have multiple different types of motion systems within different analyzer/testing stations. For example, some stations can include friction tracks for shuttling pucks or trays of sample tubes, and may include carousels containing smaller vessels, such as cuvettes and reaction vessels, into which portions of the sample can be aspirated and dispensed. In some embodiments, by integrating portions of the track system into the analyzer stations themselves, each station can include its own queuing logic and may be simplified to eliminate unnecessary internal motion systems.

With respect to FIG. 3, the track 200 can be broken into modular components that are integrated into analyzer modules. In this exemplary track, modules 205, 205A, and 205B can be combined with one another and optionally other modular track components 202 and 204 to form a track similar to that shown in FIG. 2B. For instance, 205A can be a module that performs the same function as immunoassay 110 (FIG. 1), 205 can be a module that performs the same function as low-volume chemistry module 120 (FIG. 1), and 205B can be a module that performs ISE electrolyte testing, like module 130 (FIG. 1). In this example, the main outer track can be formed by track segments 202, 204, 206, 206A, 206B, 208, 208A, and 208B. Within the analyzer modules 205, 205A, and 205B, internal paths 210, 210A, and 210B form pullouts from the main track. The internal paths can be used for internal queuing and can be managed independently within each analyzer module to allow each module to have greater control over samples to be processed.

One advantage of integrating track 200 and sub-paths 210, 210A, and 210B into the analyzer modules 205, 205A, and 205B, respectively, is that the internal handling mechanisms within each analyzer module can be specially adapted to better coordinate with the track sub-paths. In some embodiments, modules 205, 205A, and 205B can be adapted to process each sample within a period that is less than an operation cycle of the overall analyzer, leaving enough time for the sample to be routed along the track system to another module after processing, allowing the other module to immediately process the sample on the next operation cycle. As used herein, an operation cycle is a unit of time used by scheduling algorithms to allot processing time to modules for sample assays. These can be dynamic or fixed and can allow synchronous operation of the modules in the analyzer and provide a reliable timing model for scheduling samples amongst multiple modules in the analyzer. The operation cycle time can be chosen to be the time needed by any given module between when it starts processing a first sample, and when it is ready to process another sample under expected steady-state conditions. For example, if an analyzer can process one test every three seconds, and the expected average tests per sample is seven, the operation cycle time can be 21 seconds. It should be understood that individual modules can implement efficiency techniques, such as parallelism or processing multiple samples within a cycle, to maximize throughput, even when the number of tests-per-sample varies from an expected amount. Furthermore, it should be understood that in some embodiments, individual modules have different operation cycle times, and these modules can operate substantially asynchronously from one another. Virtual queues or buffers can be used to assist the management of sample scheduling where cycle times or demand vary between modules.

Enabling transit between modules in the analyzer in a reliable time frame, on the order of a single operation cycle or less, achieves many performance advantages not possible with prior art track systems. If a sample can be reliably handled by an analyzer module and transported to the next analyzer module within a single cycle of the analyzer, traffic handling in queuing becomes much simpler, throughput becomes more consistent, and latency can be controlled and reduced. Essentially, in such an analyzer, a sample can reliably be handled by the track system and processed uniformly such that a sample does not sit idly on the track system waiting in queues. Furthermore, queues within the system, such as queues within a given analyzer module, can reliably be shortened, limited by the number of modules within the system.

In some embodiments of the present invention, the reliable and rapid nature of the track system enables queues to be virtual, rather than physical. A virtual queue can be handled in software, rather than by physical limitations. Traditionally, queues have been physical. The simplest physical queue is effectively a traffic jam at any given part of a sample handling operation. A bottleneck creates a first-in first-out (FIFO) queue, where sample carriers are effectively stopped in a line, providing a buffer so that an analyzer or a decision point can request the next sample in the queue when it is ready. Most prior art lab automation tracks maintain FIFO processing queues to buffer samples that are waiting to be processed by the attached modules (analyzers or pre/post analytic devices). These buffers allow the track to process sample tubes at a constant rate, even though the modules or operator requests can create bursts of demand. FIFO queues can also substantially increase the throughput of the individual modules by allowing them to perform preprocessing tasks for future samples, for example, prepare a cuvette or aspirate reagent, while processing the current sample. While the rigid predictability of FIFO queues enables the parallelization of some processing tasks, it also can prevent the modules from using opportunistic scheduling that may increase throughput by reordering tests on samples to optimize resources. For example, the internal resource conflicts of most immunoassay analyzers can be so complex that the analyzers need to interleave the tests from multiple samples in order to reach maximum efficiency. A FIFO queue can reduce the throughput of these analyzers by as much as 20%. Another challenge with FIFO queues is their inability to handle priority samples (e.g., a STAT sample). If a STAT sample needs to be processed immediately, the entire FIFO queue has to be flushed back onto the main track, delaying all other samples on the track and forcing the original module to slowly rebuild its queue.

Another type of queue is a random access (RA) queue. A carousel is an example of a physical RA queue found in analyzer modules. By aliquoting a portion of a sample into one or more vessels in a carousel ring, an analyzer module can select any of a number of samples to process at any time within the analyzer. However, carousels have many drawbacks, including added complexity, size, and cost. A carousel also increases the steady-state processing time, because a sample must be transferred into and out of the random-access queue. Processing delays depend on the implementation, such as the number of positions in a carousel. On the other hand, by having random access to samples, a local scheduling mechanism within a module can process samples in parallel, performing sub-steps in any order it desires.

In some embodiments, carousels or other RA queues can be eliminated from the modules and the sub-paths (e.g., 210) from the automation system can be used as part of an RA or FIFO queue. That is, if the travel time for a sample between any two points can be bounded to a known time that is similar to that of a carousel, (such as predictably less than a portion of an operation cycle), the track 200 can be part of the queue for a given module. For example, rather than using a carousel, module 205 can utilize samples in carriers on sub-path 210. Preprocessing steps, such as reagent preparation, can be conducted prior to the arrival of a sample under test. Once that sample under test arrives, one or more portions of the sample can be aspirated into cuvettes or other reaction vessels for an assay. In some embodiments, these reaction vessels can be contained within module 205, off track, while in other embodiments, these reaction vessels can be placed in carriers on sub-path 210 to allow easy motion. If the sample under test is required to be at a module for longer than an operation cycle, or if multiple samples will be processed by the module during an operation cycle, the sub-path 210 can act as a queue for the module.

Furthermore, samples not yet under test, which may be currently located at other modules, can be scheduled for the next operation cycle. These next-cycle samples can be considered as residing in a virtual queue for module 205. A module can schedule samples to arrive during a given operation cycle for any sample on track 200. A central controller, or controllers associated with modules themselves, can resolve any conflicts over a sample for a given cycle. By giving a module a prior knowledge of the arrival time of a sample, each module can prepare resources and interleave tests or portions of tests to more efficiently allot internal resources. In this manner, modules can operate on samples in a just-in-time manner, rather than using large physical buffers. The effect is that the virtual queue for a given module can be much larger than the physical capacity of the sub-path serving that module, and existing scheduling algorithms can be used. Effectively, each module can treat track 200 as it would treat a sample carousel in a prior art module.

It should be appreciated that, by employing virtual queues in some embodiments, multiple modules can have multiple queues and can share a single queue or samples within a queue. For example, if two modules are equipped to perform a certain assay, a sample needing that assay can be assigned to a virtual queue for that assay, which is shared between the two modules capable of handling the assay. This allows load balancing between modules and can facilitate parallelism. In embodiments where reaction vessels are placed in carriers on track 200, an assay can be started at one module (e.g., reagents prepared and/or sample mixed in) and the assay can be completed at another (e.g., a reaction is observed at another module). Multiple modules can effectively be thought of as a multi-core processor for handling samples in some embodiments. In these embodiments, scheduling algorithms for the multiple modules should be coordinated to avoid conflicts for samples during a given operation cycle.

By employing virtual queues, modules can operate on samples while the samples are in the virtual queues of other modules. This allows low latency of samples, as each sample that is placed onto track 200 can be processed as quickly as the modules can complete the tests, without having to wait through a physical queue. This can greatly reduce the number of sample carriers on track 200 at any given time, allowing reliable throughput. By allowing modules to share queues or samples, load balancing can also be used to maximize throughput of the system.

Another advantage of using virtual queues is that STAT samples can be dynamically assigned priority. For example, a STAT sample can be moved to the head of any queue for the next operation cycle in software, rather than having to use a physical bypass to leapfrog a STAT sample to the head of a largely static physical queue. For example, if a module is expecting three samples to be delivered by track 200 for assays during the next operation cycle, a scheduler responsible for assigning samples to the module can simply replace one or more of the samples with the STAT sample, and have the track 200 deliver the STAT sample for processing during the next operation cycle.

If decision points such as 214 and 216 can be streamlined such that there is no need for a queue at each decision point, the only physical queues can be within sub-paths 210, 210A, and 210B. As described above, these can be treated as RA queues or FIFO queues. If a STAT sample is placed onto track 200, RA queues within sub-paths 210, 210A, and 210B need not be flushed, as the STAT sample can be processed immediately. Any FIFO queues can be individually flushed. For example, if a STAT sample is placed onto track 200 at section 222, the sample may be routed to the appropriate analyzer 205B via the outside track and decision point 216. If there are other samples (and by extension the sample carriers transporting those samples) waiting in the queue in path 210B, only those samples in the queue may need to be flushed to allow a STAT sample to take priority. If the outer track 200 is presumed to take less than an operation cycle to traverse, any samples that were flushed from the queue in 210B can simply be circulated around the track and placed immediately back into the queue in path 210B immediately behind the STAT sample, eliminating any down time caused by the STAT sample.

Entry paths 220 and 222 can be used to input samples to the track 200. For example, regular priority samples can be placed onto track 200 at input 220 and STAT priority samples can be placed on input 222. These inputs can be used as outputs for samples when complete, or other ports (not shown) can be used as the output paths for used samples. Input 220 can be implemented as an input buffer, acting as a FIFO queue for input samples seeking access to the track 200. Once a sample reaches the head of the queue at input 220, it can be moved onto the track (either by being placed in a carrier or by being placed in a carrier when it is placed in input 220). A STAT sample can enter the track 200 immediately after being placed at input 222 or, if track 200 is overcrowded, the STAT sample can enter the track at the next available uncrowded operation cycle. Some embodiments monitor the number of carriers on the track during an operation cycle and limit the total number to a manageable amount, leaving the remainder in input queues. By restricting samples at the input, track 200 can be free of traffic, allowing it to always be operated in the most efficient manner possible. In these embodiments, the transit time of a sample between two modules can be a bounded value (e.g., less than some portion of an operation cycle), allowing simplified scheduling.

In some embodiments, the track system 200 can be designed to be bidirectional. This means that sample carriers can traverse the outside path and/or any sub-paths in either direction. In some embodiments, additional sub-paths, such as 211B accessed via additional decision points 215 and 217, can assist in providing bidirectional access. Bidirectional paths can have inherent advantages. For example, if normal priority samples are always handled in the same direction, a STAT sample can be handled in the opposite direction along the sub-path. This means that a STAT sample can essentially enter the exit of the sub-path and be immediately placed at the head of the queue without requiring the queue to be flushed. For example, if a STAT sample is placed on track 200 at segment 204, it can enter path 210B via decision point 214 and proceed into path 210B to be immediately placed at the head of any queue. Meanwhile, in all of these examples, because queues are presumed to be limited generally to sub-paths, there is no need to flush queues in other modules if a STAT sample does not need immediate access to those modules. Any additional modules that need to service a STAT sample on a subsequent cycle can flush their queues at that point, providing "just-in-time" access to a STAT sample without otherwise disrupting the operation of each analyzer module.

Modular design also allows certain other advantages. If the automation systems within an analyzer module are adapted to take advantage of the track system contained in the module, new features can be added that use the common track. For example, a module could have its own internal reagent carousel that includes all of the reagents necessary for performing the assays prescribed for the samples. When reagents stocked in the analyzer module run low, an operator can replenish the reagents in some embodiments by simply loading additional reagents onto carriers on the track 200. When the reagents on track 200 reach the appropriate module, the module can utilize mechanical systems such as an arm or a feeder system that takes the reagents off of the track and places the reagents in the reagents store for the module.

In some embodiments, the individual track portions shown in FIG. 3 and FIG. 2A and FIG. 2B can be operated independently from one another, or can be passive. Independent carrier movement provides advantages over friction-based track systems, such as non-localized conveyor belts where the entire friction track must be moved to effect movement of a sample carrier. This means that other samples also on that track must move at the same rate. This also means that if certain sections operate at different speeds, collisions between passive carriers carrying samples can occur.

FIG. 4A depicts an exemplary carrier 250 for use with the present invention. Carrier 250 can hold different payloads in different embodiments. One payload can be a sample tube 255, which contains a fluid sample 256, such as blood or urine. Other payloads may include racks of tubes or reagent cartridges or any other suitable cartridge. Sample carrier 250 includes a main housing body 260, which can house the internal electronic components described herein. The main housing body 260 supports a bracket 262, which can accept a payload. In some embodiments, this is a shallow hole that is designed to accept a fluid container 255 such as a sample tube, and hold it with a friction fit. In some embodiments, the friction fit can be made using an elastic bore or a clamp that can be fixed or energized with a spring to create a holding force. In some embodiments, sample racks and reagent cartridges can be designed to also attach to the bracket 262, allowing bracket 262 to act as a universal base for multiple payload types.

Body 260 can include or be coupled to guide portion 266, which allows the carrier 250 to follow a track between decision points. Guide portion 266 can include, for example, a slot to accept one or more rails in the track, providing lateral and/or vertical support. In some embodiments, the guide portion allows the carrier 250 to be guided by walls in the track, such as the walls of a trough-shaped track. The guide portion 266 can also include drive mechanisms, such as friction wheels that allow a motor in the carrier body 260 to drive the carrier or puck 250 forward or backward on the track. The guide portion 266 can include other drive components suitable for use with the embodiments described throughout, such as magnets or induction coils.

Rewritable display 268 can be provided on the top of the carrier 250. This display can include an LCD oriented panel and can be updated in real time by the carrier 250 to display status information about sample 256. By providing the electronically rewritable display on the top of the carrier 250, the status information can be viewed at a glance by an operator. This can allow an operator to quickly determine which sample he/she is looking for when there are multiple carriers 250 in a group. By placing the rewritable display on top of the carrier 250, an operator can determine status information even when multiple carriers 250 are in a drawer or rack.

Figure 4B:
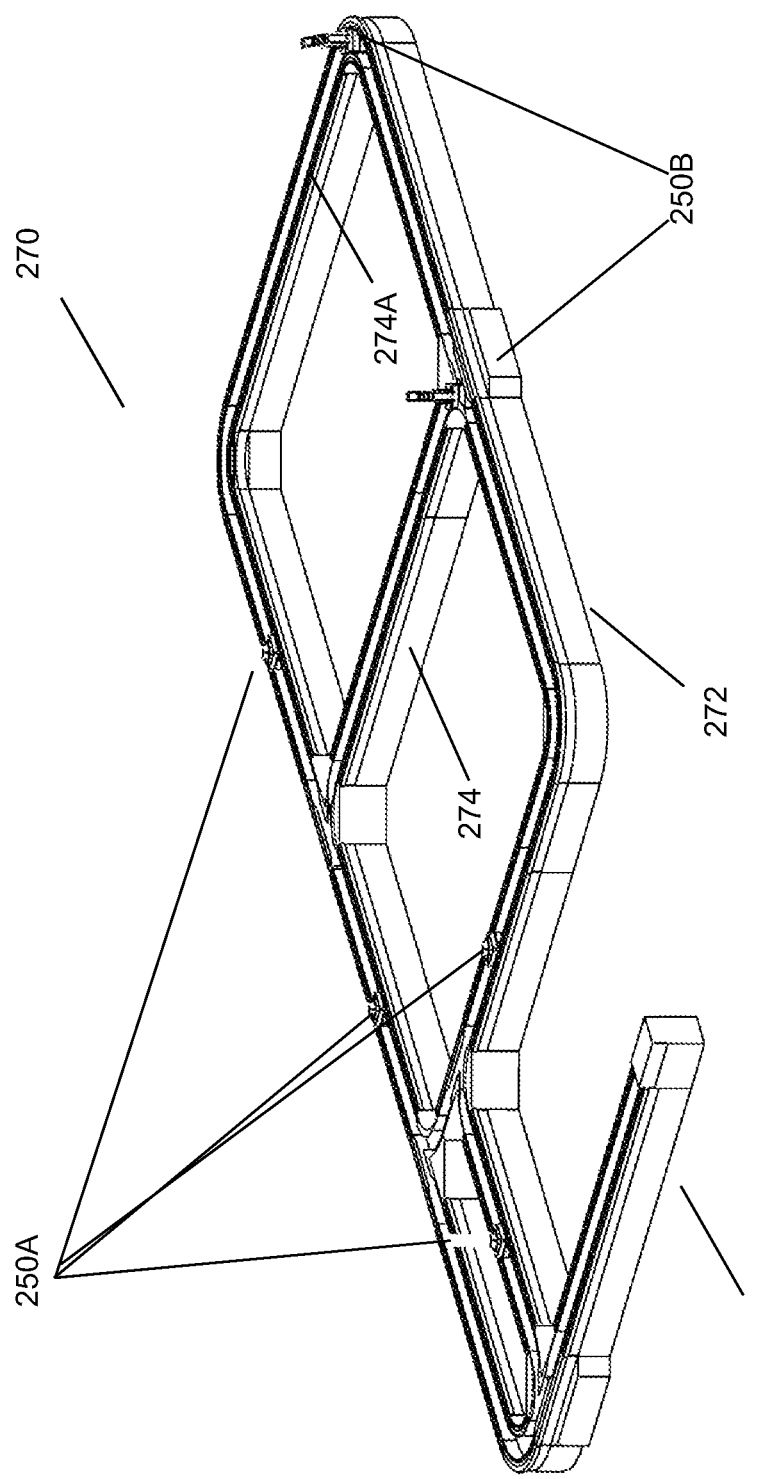
FIG. 4B is a perspective view of an exemplary track configuration that can be used with the embodiments disclosed herein.

FIG. 4B shows an exemplary track configuration 270 for use by carriers 250. In this example, carriers 250A transport sample tubes, while carriers 250B transport racks of tubes along main track 272 and/or subpaths 274 and 274A. Path 276 can be used by an operator to place samples into carriers or remove samples from these carriers.

Figure 4C:
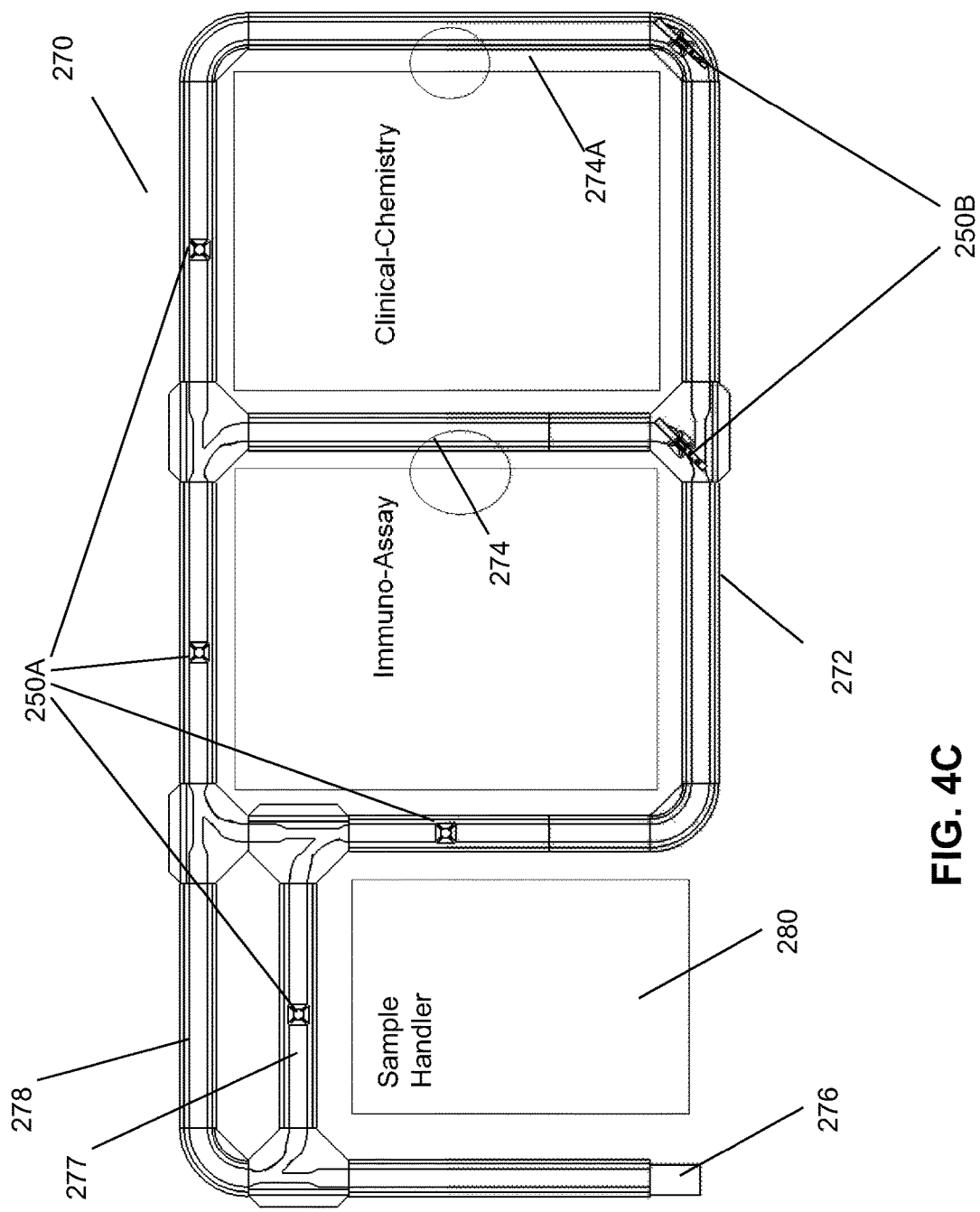
FIG. 4C is a top view of an exemplary automation system that can be used with the embodiments disclosed herein.

FIG. 4C shows an additional view of an exemplary track configuration 270. In this example, sub-path 274 serves an immunoassay station, while sub-path 274A serves a clinical chemistry station. Input/output lane 276 can be served by a sample handler station 280 that uses sub-paths 277 and 278 to buffer samples for insertion or removal of the samples from the main track 272.

In some embodiments, the sample handler 280 can also load and unload samples or other payloads to/from the carriers 250A and 250B. This allows the number of carriers to be reduced to the amount needed to support payloads that are currently being used by the stations in track system 270, rather than having a vast majority of carriers sitting idle on tracks 277 and 278 during peak demand for the analyzer. Instead, sample trays (without the carriers disclosed herein) can be placed/removed by an operator at input/output lane 276. This can reduce the overall cost of the system and the number of carriers needed can be determined by the throughput of the analyzer, rather than based on anticipating the peak demand for the analyzer in excess of throughput.

Intelligent Carriers

Whereas some embodiments may utilize passive pucks or trays (e.g., the puck is a simple plastic or rubber brick that lacks active or autonomous systems, power, onboard processing, or control) to reduce cost and complexity, in some embodiments the added complexity and cost necessary to integrate intelligence and autonomy into individual carriers (which can include smart pucks or trays in some embodiments) can provide certain benefits. Accordingly, embodiments of the present invention can utilize intelligent carriers to enable certain improvements over passive pucks on the friction-based tracks. For example, one disadvantage of prior art track systems is that, at each decision point, the decision for directing a puck is made by the track by rotating the puck and reading a barcode optically. Rotating and optical reading is a relatively slow process. Furthermore, this process can be redundant because the system has a prior knowledge of the identification of the sample tube when the sample tube is placed into the puck by an operator. Embodiments of the present invention can include carriers that have means to identify the contents of the sample tube (and optionally communicate this information to the automation system) without requiring the carrier to be stopped, rotated, and read optically.

For example, a carrier can include an onboard optical reader to automatically read a barcode of a payload. The results of the scan can then be stored in the memory of a carrier if the carrier has onboard processing capability. Alternatively, an outside source, such as a hand barcode reader operated by an operator at the time of placing the sample into the carrier, can communicate the barcode information of the payload to the carrier via RF signal or other known means, such as a communication protocol using temporary electrical contact or optical communication. In some embodiments, the association of the carrier with the payload can be stored external to the carrier and the identity of the carrier can be conveyed by the carrier to the system by RF, optical, or near-field communication, allowing the system to assist in routing or tracking the carrier and the payload. Routing decisions can then be made by the carrier or by identifying the carrier, rather than reading a unique barcode of a payload.

By moving processing capability and/or sensor capability onto each individual carrier, the carriers can participate actively and intelligently in their own routing through the track system. For example, if individual carriers can move independently of one another either by autonomous motive capabilities or by communication with the track, certain performance advantages can be realized.

By allowing carriers to move independently, carriers can move around the track faster. One key limitation on the motion of a carrier is that it should not spill an open-tube sample. The limiting factor is generally not the velocity of the carrier in a straight line, but the acceleration and jerk experienced by the carrier (while speeding up, slowing down, or turning), which may cause splashing. For prior art friction-based track systems, the velocity of the track is typically limited to prevent acceleration and jerk experienced by pucks from exceeding threshold amounts because the entire track moves. However, by using a track system with independently operating sections that can respond to individual carriers, or individual carriers that have independent motive capability, the acceleration of any given carrier can be tailored to limit acceleration/deceleration and jerk, while allowing the average velocity to be greater than that of traditional tracks. By not limiting the top speed of a carrier, the carrier can continue to accelerate on each track section as appropriate, resulting in a substantially higher average speed around the track. This can assist the carrier in traversing the entire track system in less than one machine cycle of the analyzer. These machine cycles can be, for instance 20 or 40 seconds.

Similarly, an autonomous carrier can know its own identity and that of its payload. This allows the carrier to actively participate or assist in the routing decision process at individual decision points. For example, upon reaching a decision point (e.g., switch, intersection, junction, fork, etc.), a carrier can communicate its identity and/or the identity of its payload to the track or any switching mechanism (or its intended route that the carrier has determined based on the payload identity), via RF or near-field communication. In this scenario, the carrier does not need to be stopped at a decision point for a barcode scan. Instead, the carrier can keep going, possibly without even slowing down, and the carrier can be routed in real time. Furthermore, if the carrier knows where it is going or communicates its identity to the track (such that the track knows where the carrier is going) before the carrier physically reaches a decision point, the carrier can be made to decelerate prior to a decision point if the carrier will be turning. On the other hand, if the carrier does not need to turn at the decision point, the carrier can continue at a higher velocity because the sample carried by the carrier will not undergo cornering forces if the carrier is not turning at the decision point or a curved section of the track.

An autonomous carrier can also include onboard processing and sensor capabilities. This can allow a carrier to determine where it is on the track and where it needs to go, rather than being directed by the track (although, in some embodiments, a central controller sends routing instructions to the carrier to be carried out). For example, position encoding or markers in the track can be read by a carrier to determine the carrier's location. Absolute position information can be encoded on a track surface to provide reference points to a carrier as it traverses the track. This position encoding can take many forms. The track may be encoded with optical markers that indicate the current section of the track (e.g., like virtual highway signs), or may further include optical encoding of the specific absolute location within that section of track (e.g., like virtual mile markers). Position information can also be encoded with markings between absolute position marks. These can provide synchronization information to assist a carrier in reckoning its current trajectory. The optical encoding scheme may take on any appropriate form known to one skilled in the art. These marks used by the encoding scheme may include binary position encoding, like that found in a rotary encoder, optical landmarks, such as LEDs placed in the track at certain positions, barcodes, QR codes, data matrices, reflective landmarks, or the like. General position information can also be conveyed to the carrier via RF/wireless means. For example, RFID markers in the track can provide near field communication to the carrier to alert the carrier that it has entered a given part of the track. In some embodiments, local transmitters around or near the track can provide GPS-like positioning information to enable the carrier to determine its location. Alternatively, sensors in the track, such as Hall effect sensors or cameras, can determine the position of individual carriers and relay this information to the carrier.

Similarly, the carrier can have sensors that indicate relative motion, which provide data that can be accumulated to determine a position between absolute position marks. For example, the carrier may have gyroscopes, accelerometers, or optical sensors that observe speckle patterns as the carrier moves to determine velocity or acceleration, which can be used to extrapolate a relative position. In some embodiments, components include a light source and an image sensor that can be used to observe the relative motion of the track surface with respect to the carrier to determine a real-time trajectory estimate. For example, after reckoning its position with an absolute position mark, the carrier can observe successive images of a track surface and compare these images to determine the direction and magnitude of motion. This can be used to determine real-time position, velocity, acceleration, and jerk, or estimates thereof. In addition, synchronous marks, such as marks placed at regular intervals in the track, can be used to reckon the carrier's position between absolute position marks and can correct errors that may have accumulated in the real-time trajectory information determined from observation of the relative motion of the surface of the track. This can allow a lower sampling frequency or less precise components in the position decoding imaging sensor.

Because a carrier can know where it is and its motion relative to the track, a carrier can essentially drive itself, provided it knows its destination. The routing of the carrier can be provided in many different ways in various embodiments. In some embodiments, when a carrier is loaded with the sample, the system can tell the carrier the destination analyzer station. This information can be as simple as the identification of the destination station in embodiments where the carrier has autonomous routing capability. This information can also be detailed information such as a routing list that identifies the specific path of the individual track sections and decision points that a carrier will traverse. Routing information can be conveyed to the carrier via any communication method described herein, such as RF communication, near-field/inductive communication, electrical contact communication, or optical communication.

In an exemplary embodiment, when an operator scans the barcode of the sample tube and places it in a carrier, the system determines the identity of the carrier and matches it with the identity of the sample. The system then locates the record for the sample to determine which tests the sample must undergo in the analyzer. A scheduler then allocates testing resources to the sample, including choosing which tests will be done by individual testing stations and when the sample should arrive at each testing station for analysis. The system can then communicate this schedule (or part of the schedule) to the carrier to inform the carrier of where it needs to go, and optionally when it needs to go and/or when it needs to arrive.

Once the carrier is placed onto the track system, the routing capabilities and location acquisition systems of the carrier enable the carrier to determine where it is on the track and where it needs to go on the track. As the carrier traverses the track, the carrier reaches individual decision points and can be directed along the main track or along sub-paths as appropriate. Because each carrier operates independently from one another, a carrier can do this quite quickly without necessarily stopping at each decision point and without waiting for other carriers in a queue. Because these carriers move quickly, there is less traffic on the main sections of the track, which reduces the risk of collision or traffic jams at decision points or corners in the track (e.g., sections where carriers might slow down to avoid excessive forces on the sample).

Motive force can be provided to the carriers in many ways. In some embodiments, the track actively participates in providing individualized motive force to each carrier. In some embodiments, motive force is provided by electromagnetic coils in the track that propel one or more magnets in the carrier. An exemplary system for providing this motive force is the track system provided by MagneMotion, Inc., which can generally be understood by the description of the linear synchronous motors (LSMs) found in US Published Patent Application 2010/0236445, assigned to MagneMotion, Inc. These traditional systems utilizing this magnetic motion system have included passive carriers that lack the integrated intelligence of the carriers described herein, and all routing and decisions are made by a central controller with no need for active carriers that participate in the routing and identification process.

In embodiments that utilize magnetic motion, the electromagnetic coils and the magnets operate as an LSM to propel each individual carrier in the direction chosen with precise control of velocity, acceleration, and jerk. Where each coil on the track (or a local set of coils) can be operated independently, this allows highly localized motive force to individual carriers such that individual carriers can move with their own individually tailored accelerations and velocities. Coils local to a carrier at any given moment can be activated to provide precise control of the direction, velocity, acceleration, and jerk of an individual carrier that passes in the vicinity of the coils.

In some embodiments, a track may be comprised of many individually articulable rollers that act as a locally customizable friction track. Because individual micro-sections of the track can be managed independently, rollers immediately around a carrier may be controlled to provide individualized velocity, acceleration, and jerk. In some embodiments, other active track configurations can be used that provide localized individual motive force to each carrier.

In some embodiments, the track may be largely passive, providing a floor, walls, rails, or any other appropriate limitations on the motion of a carrier to guide the carrier along a single dimension. In these embodiments, the motive force is provided by the carrier itself. In some embodiments, each individual carrier has one or more onboard motors that drive wheels to provide self-propelled friction-based motive force between the track and the carrier. Unlike traditional friction tracks, where the track is a conveyor, carriers with driven wheels can traverse the track independently and accelerate/decelerate individually. This allows each carrier to control its velocity, acceleration, and jerk at any given moment to control the forces exerted on its payload, as well as traverse the track along individually tailored routes. In some embodiments, permanent magnets may be provided in the track and electromagnets in the carrier may be operated to propel the carrier forward, thereby acting as an LSM with the carrier providing the driving magnetic force. Other passive track configurations are also contemplated, such as a fluid track that allows carriers to float and move autonomously via water jets or the like, a low friction track that allows carriers to float on pockets of air provided by the track, (e.g., acting like a localized air hockey table), or any other configuration that allows individual carriers to experience individualized motive forces as they traverse the track.

Figure 5:
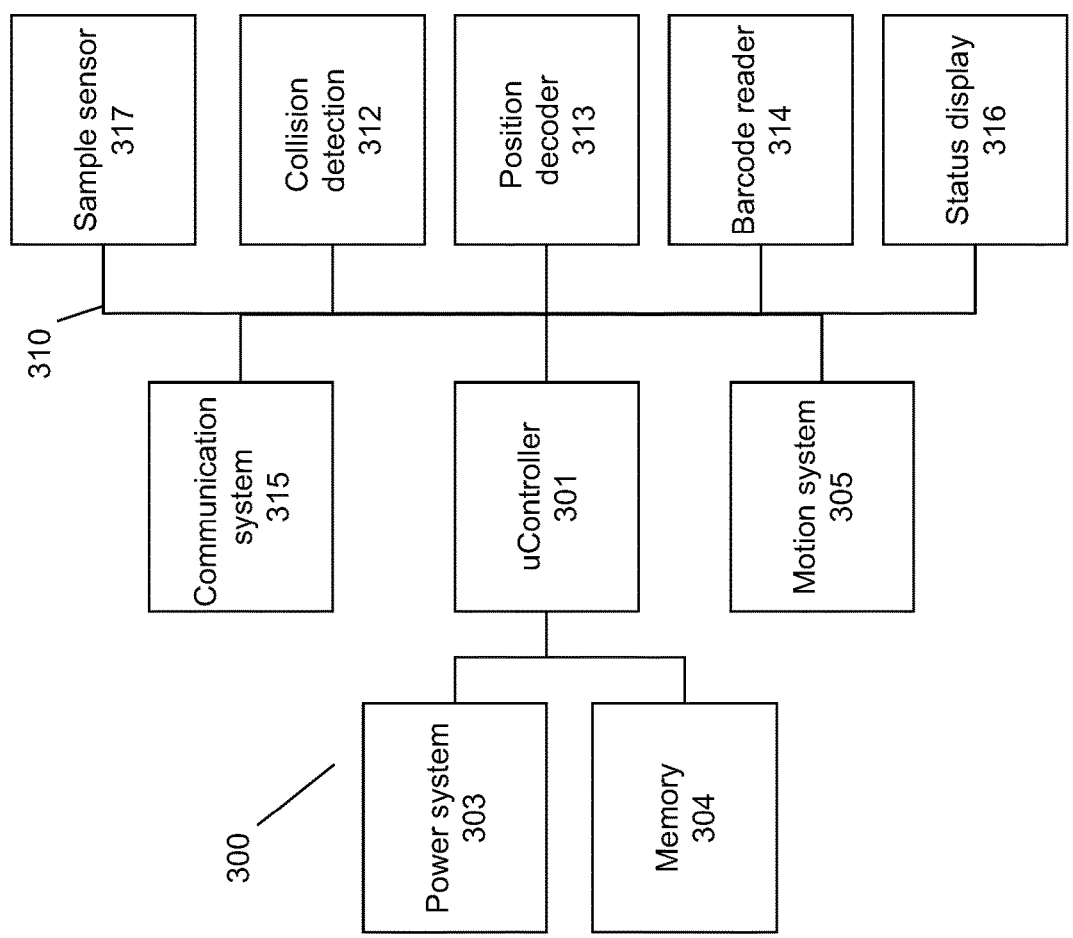
FIG. 5 is a system block diagram of the control systems including onboard active carriers that can be used with certain embodiments disclosed herein.
Figure 9A:
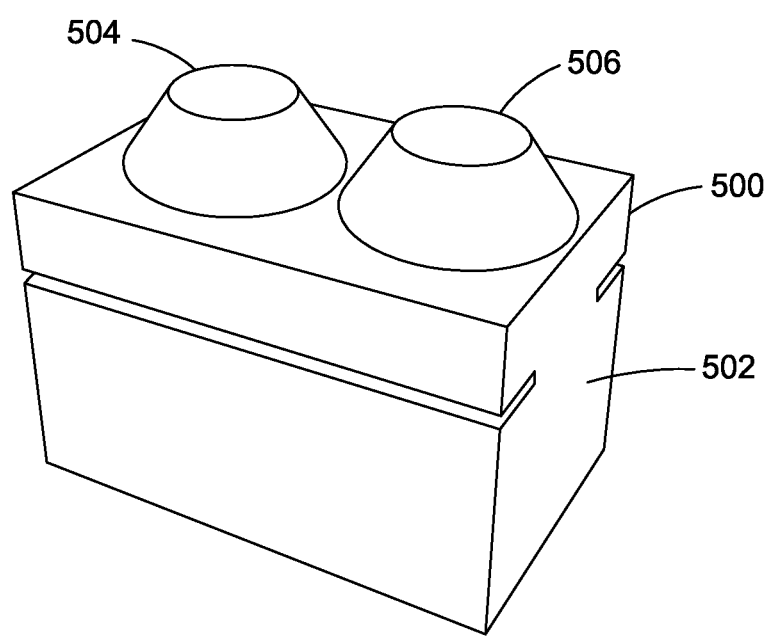
FIG. 9A is a perspective view of an exemplary carrier having two slots that can be used with the embodiments disclosed herein.

FIG. 5 shows a top level system diagram of the control systems and sensors for an intelligent autonomous carrier 300. Carrier 300 can be any suitable embodiment of a carrier, such as a carrier 250, shown at FIG. 4A, that is configured to hold a single fluid container 255 and carrier 500, shown at FIG. 9A to FIG. 9B, that is configured to hold multiple fluid containers 508, 510. Carrier 300 is controlled by an onboard processor, such as microcontroller 301 that includes sufficient processing power to handle navigation, maintenance, motion, and sensor activities needed to operate the carrier. Because the carrier is active and includes onboard electronics, unlike prior art passive carriers, the carrier includes an onboard power station. The details of this station vary in different embodiments of the present invention. In some embodiments, power system 303 comprises a battery that may be charged as the carrier operates, while, in other embodiments, the battery is replaceable or can be manually charged when the carrier is not operating. Power system 303 can include the necessary charging electronics to maintain a battery. In other embodiments, the power system 303 comprises a capacitor that may be charged by inductive or electrical contact mechanisms to obtain electrical potential from the track itself, in much the same way a subway car or model train might receive power.

Microcontroller 301 communicates with system memory 304. System memory 304 may include data and instruction memory. Instruction memory in memory 304 includes sufficient programs, applications, or instructions to operate the carrier. This may include navigation procedures as well as sensor handling applications. Data memory in memory 304 can include data about the current position, speed, acceleration, payload contents, navigational plan, identity of the carrier or payload, or other status information. By including onboard memory in carrier 300, the carrier can keep track of its current status and uses information to intelligently route around the track or convey status information to the track or other carriers.

Microcontroller 301 is responsible for operating the motion system 305, sensors 312, 313, and 314, communication system 315, status display 316, and sample sensor 317. These peripherals can be operated by the microcontroller 301 via a bus 310. Bus 310 can be any standard bus, such as a CAN bus, that is capable of communicating with the plurality of peripherals, or can include individual signal paths to individual peripherals. Peripherals can utilize their own power sources or the common power system 303.

Motion system 305 can include the control logic necessary for operating any of the motion systems described herein. For example, motion system 305 can include motor controllers in embodiments that use driven wheels. In other embodiments, motion system 305 can include the necessary logic to communicate with any active track systems necessary to provide a motive force to the carrier 300. In these embodiments, motion system 305 may be a software component executed by microcontroller 301 and utilizing communication system 315 to communicate with the track. Devices such as motors, actuators, electromagnets, and the like, that are controlled by motion system 305 can be powered by power system 303 in embodiments where these devices are onboard the carrier. External power sources can also provide power in some embodiments, such as embodiments where an LSM provides motive force by energizing coils in the track. In some embodiments, motion system 305 controls devices on or off the carrier to provide motive force. In some embodiments, the motion system 305 works with other controllers, such as controllers in the track, to coordinate motive forces, such as by requesting nearby coils in the track be energized or requesting the movement of local rollers. In these embodiments, motion system 305 can work together with communication system 315 to move the carrier.

Carrier 300 can include one or more sensors. In some embodiments, carrier 300 includes a collision detection system 312. Collision detection system 312 can include sensors at the front or back of a carrier for determining if it is getting close to another carrier. Exemplary collision detection sensors can include IR range-finding, magnetic sensors, microwave sensors, or optical detectors. Whereas many prior art pucks are round, carrier 300 may be directional, having a front portion and a rear portion. By having a directional geometry, carrier 300 can include a front collision detector and a rear collision detector.

In some embodiments, collision detection information can include information received via the communication system 315. For example, in some embodiments, the central controller for the track can observe the location and speed of carriers on the track and evaluate collision conditions and send updated directions to a carrier to prevent a collision. In some embodiments, nearby carriers can communicate their positions in a peer-to-peer manner. This allows carriers to individually assess the risk of collision based on real-time position information received from other carriers. It will be understood that in embodiments where the carrier receives trajectory information about other carriers, or decisions are made with the help of a centralized controller that has access to trajectory information of nearby carriers, the carriers need not be directional, and can include sensors or receivers that do not depend on a given orientation of a carrier.

Carrier 300 can also include a position decoder 313. This sensor can extrapolate the carrier's position as described herein. For example, position decoder 313 can include a camera or other optical means to identify landmarks in the track, or observe optical encoding in the track. In some embodiments, position decoder 313 can also include inertial sensors, magnetic sensors, or other sensors sufficient to determine a carrier's current position, direction, velocity, acceleration, and/or jerk.

Carrier 300 can optionally include a barcode reader 314. If equipped with the barcode reader 314, carrier 300 can observe the barcode of its payload at the time the samples are loaded onto the carrier or at any time thereafter. This prevents the need for a carrier to stop at individual decision points to have the system read the barcode of a sample tube. By reading and storing the identity of the sample tube, or conveying this information to the overall system, a carrier may more efficiently traverse the track system because routing decisions can be made in advance of reaching a decision point. Alternatively, where a system knows the identity of the sample when it is placed onto the carrier, the system can include an external barcode reader and can convey the identity of the payload to the carrier for storage and memory 304 via communication system 315.

Communication system 315 can comprise any mechanisms sufficient to allow the carrier to communicate with the overall automation system. For example, this can include an XBee communication system for wireless communication using an off-the-shelf communication protocol, such as 802.15.4, any appropriate version of 802.11, or any standard or proprietary wireless protocol. Communication system 315 can include a transceiver and antenna and logic for operating an RF communication protocol. In some embodiments, communication system 315 can also include near-field communication, optical communication or electrical contact components. Information conveyed via the communications system to/from carrier 300 is described throughout this application.

In some embodiments, the carrier can also include a status display module 316. The status display module 316 can include a controller and rewritable electronic display, such as an LCD panel or E-ink display. In some embodiments, the controller is treated as an addressable portion of memory, such that the microcontroller 301 can easily update the status display 316.

In some embodiments, the carrier also includes sample sensor 317. This sensor can be used to indicate the presence or absence of a fluid container in the carrier's tube bracket (which may also be referred to as a tube holder). In some embodiments, this is a momentary mechanical switch that is depressed by the presence of a tube and not depressed when a tube is absent. This information can be used to determine the status of a tube, which can assist in the display of status information by status display module 316.

Routing

The desire for rapid transit times within an analyzer system can make routing difficult. In prior art systems, rapid routing is less critical because samples are generally stopped, singulated, and scanned at each decision point. In those systems, the routing decision for a given decision point can be made while the sample is stopped. Rapid routing decisions are generally desired, and may require determining a switching decision before a sample carrier reaches a decision point. Furthermore, because the carriers move at a rapid rate compared to the prior art, the control of the instantaneous trajectory of a sample carrier can be assisted by real-time processing in order to prevent spilling or damaging IVD samples. In some embodiments, substantially instantaneous trajectory observation and control is conducted onboard each carrier to facilitate real-time control, while the overall routing decisions are made by a central controller that manages a group of carriers. Therefore, in some embodiments of the present invention, the carriers act like semi-autonomous robots that receive global routing instructions from a central controller, but make local motion decisions substantially autonomously.

For example, when a carrier receives a sample (e.g., a patient fluid sample or other payload) a central controller managing one or more carriers determines the schedule for that carrier and instructs the carrier where to go on the track of, for example, an in-vitro diagnostics automation system. This instruction can be a next-hop instruction (e.g., identifying the next leg of a route), such as going to a given decision point, moving forward to the next decision point, or turning at a given decision point. In some embodiments, the instructions can include a complete or partial list of track segments and decision points to be traversed and whether to turn at each decision point. These instructions can be communicated to the carrier from a central controller via any conventional means, including wireless or contact electrical signaling, as explained throughout this disclosure.

While following the instructions, each carrier can make a determination of the appropriate velocity, acceleration, and jerk (as used herein, acceleration includes deceleration). This can include a real-time decision of whether the carrier must slow down to avoid collision or to enter a curve without causing excessive lateral forces, or slow down before the next decision point. These decisions can be made with the assistance of any onboard sensors, as well as external information received by the carrier, such as information about the position and trajectory of nearby carriers. For example, accelerometers and/or track encoding information can be used to determine the current velocity, acceleration, and jerk, as well as the current position of a carrier. This information can be used by each carrier to determine its trajectory and/or can be conveyed to other carriers. Collision detectors, such as RF rangefinders, can determine whether or not a potential collision condition exists to assist the carrier in determining whether it needs to slow down and/or stop.

This collision determination can include trajectory information about the current carrier, as well as the trajectory information about surrounding carriers received by the current carrier through observation or by receiving information from a central scheduler for the track.

Figure 6:
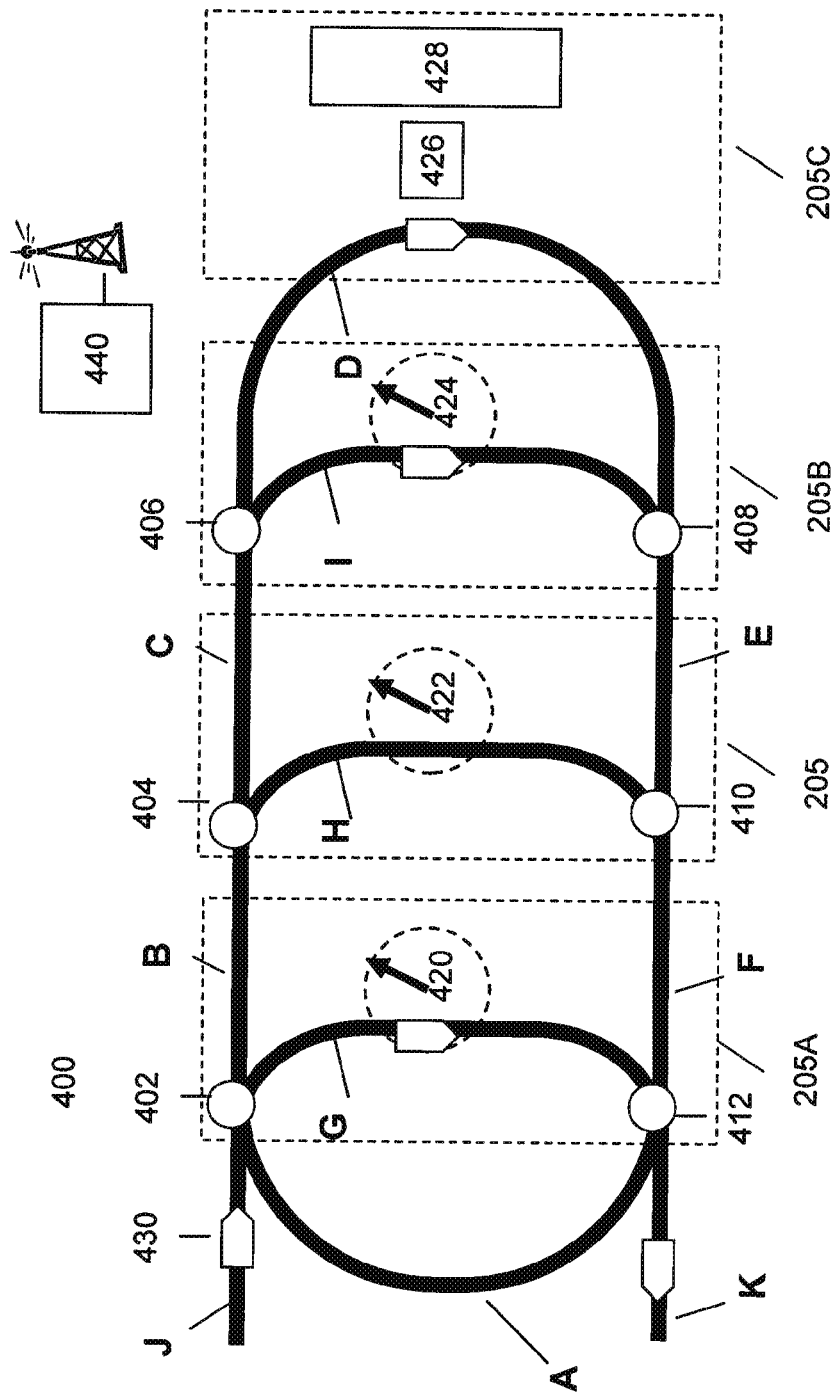
FIG. 6 is a diagrammatic view of exemplary routes in an exemplary track configuration that can be used for navigation of sample carriers in certain embodiments.

FIG. 6 shows an exemplary routing scenario in automation track system 400. Carrier 430 receives routing instructions from central management processor 440 via RF signaling. Central management processor 440 can participate in monitoring and directing carriers, including issuing routing instructions and scheduling the movement and dispatch of carriers. Central management processor 440 can be part of the central controller and/or local controllers that interact with individual modules or stations. Central or local controllers can also act at the direction of central management processor 440. Central management processor 440 can include one or more processors operating together, independently, and/or in communication with one another. Central management processor 440 can be a microprocessor, software operating on one or more processors, or other conventional computer means suitable for calculating the schedule for multiple carriers within the track system 400.

Central management processor 440 can receive position information from multiple carriers, as well as any sensor information from sensors in the track system 400 and/or information reported by the carriers. Carrier 430 can be any suitable embodiment of a carrier, such as carrier 300, shown in FIG. 5 and carrier 500, shown at FIG. 9A to FIG. 9D. Central management processor 440 uses the status information of the carriers and track as well as the identity of samples or other payload carried by the carriers and the required assays to be performed by the system on these samples.

The exemplary track 400 shown in FIG. 6 includes a first curve segment A, that connects to straight segment B and a pullout segment G, (e.g., a segment that serves a testing station), which serves analyzer/testing station 205A and pipette 420, via decision point 402. Segment B connects to straight segment C and a pullout segment H, which serves analyzer/testing station 205 and pipette 422, via decision point 404. Segment C connects to curved segment D, which serves sample handling station 205C, and pullout segment I, which serves analyzer/testing station 205B and pipette 424, via decision point 406. Segment D connects to straight segment E and the other end of pullout segment I, via decision point 408. That is, there are different paths between decision points 406 and 408—segments D and I, (where segment I is a pullout that can be used to deliver samples to interact with pipette 424). Segment E connects to straight segment F and the other end of pullout segment H, via decision point 410. Segment F connects to curved segment A and the other end of pullout segment G, via decision point 412. In some embodiments, track 400 includes input and output lanes J and K, which can be used to add or remove carriers at decision points 402 and 412.

In some embodiments, decision points 402-412 are passive forks in the track that carrier 430 can navigate to select a proper destination segment. In other embodiments, decision points 402-412 are active forks that can be controlled by carrier 430 or central management processor 440. In some embodiments, decision points 402-412 are electromagnetically controlled switches that respond to requests by carrier 430, such as via RF or near-field communication. In some embodiments these electromagnetically controlled switches have a default position, such as straight, that the switch will return to once a carrier has been routed. By using default positions for decision points, a carrier may not need to request a position at each decision point, unless it needs to be switched at that decision point.

Scheduler central management processor 440 assigns carrier 430 a first route, Route 1, to place the carrier 430 and its payload within reach of pipette 420. Carrier 430 is instructed to travel along segment J to decision point 402 and travel onto segment G to stop at a position accessible to pipette 420. In some embodiments, carrier 430 receives the instructions and determines its current location and trajectory to determine a direction and trajectory to use to reach decision point 402. Carrier 430 can also take into account that it will be making a hard right turn at decision point 402 onto segment G. In some embodiments, decision point 402 includes a switching mechanism in the track that can operate under the control of carrier 430. In these embodiments, carrier 430 communicates with the track on approach to decision point 402 to request switching onto segment G. In other embodiments, carrier 430 may have a steering mechanism (such as moveable guide wheel, directional magnets, asymmetric brakes, or the like) that allows carrier 430 to make a right turn onto segment G at decision point 402, without the assistance of an external gate integrated into the track. In these embodiments, carrier 430 engages the steering mechanism at decision point 402 to make the turn onto segment G.

This determination can be based on observing the position encoding in the track, including consulting the onboard memory of the last known position. Near-field communication from the track can also be used to provide an identification of the current track and encoding scheme being used by the track. Carrier 430 can take into account that it will be making a hard right turn at decision point 402 onto segment G. Using position encoding, carrier 430 can determine where it is in relation to decision point 402 on track J and adjust this trajectory accordingly, to ensure that it approaches the decision point with appropriate velocity.

Carrier 430 can determine its rough location—its current track section, such as section J, by reading encoding in the track, such as optical encoding, or RFID tags. In some embodiments, carrier 430 uses multiple means to determine its location within the track system 400. For example, RFID tags can be used to determine generally on which track segment the carrier 430 is located, while optical encoding or other precise encoding can be used to determine the position within that track segment. This encoding can also be used to determine velocity, acceleration, or jerk by observing changes in the encoding (e.g., derivatives from the position information).

Carrier 430 can use the identification of the current track section to determine the appropriate route to the destination section either by explicit instruction received by the central management processor 440 or by looking up an appropriate route in an onboard database in memory 304, as shown in the onboard control systems in FIG. 5. In some embodiments, the carrier 430 has an understanding of how to reach section G from section J based on a map stored in the memory of carrier 430 in memory 304. This map can include a simple lookup table or a tree of track sections where each node is linked by the corresponding decision points, or vice versa. For example, upon identifying that the carrier is currently in the track section J, the onboard database can inform carrier 430 to proceed to decision point 402 to be switched to the right onto section G.

As shown in FIG. 6, carrier 430 responds to instructions for Route 1 by proceeding onto section G and stopping at a position near pipette 420. Once the carrier 430 is stopped, it can receive additional instructions from the analyzer/testing station controlling pipette 420. For example, analyzer 205A can control pipette 420 and can instruct carriers on section G to position themselves at precise points along section G. This allows analyzer/testing stations to treat track sections as random access queues. For example, once carrier 430 stops on section G, additional instructions can be conveyed via central management processor 440 or directly from analyzer 205A to the carrier 430 via RF transmission or other means, such as local optical or inductive/near-field signals. These instructions can include halting while another carrier interacts with pipette 420, and subsequently proceeding to a position accessible to pipette 420, when analyzer 205A is ready to perform one or more assays on the sample carried by carrier 430.

Once analyzer/testing station 205A has finished interacting with the sample carried by carrier 430, additional routing instructions can be sent to the carrier 430 from the central management processor 440. For example, Route 2 can include routing instructions to proceed to section H to interact with pipette 422. In some embodiments, the routing tables contained within onboard memory 304 of carrier 430 have sufficient information about the track layout to allow the carrier to route itself to section H. In other embodiments, a list of routing steps can be transmitted to carrier 430 via central management processor 440. It will be appreciated that other embodiments can include conveying any subset of the route to carrier 430 and/or sending routing instructions in a piecemeal fashion, such that carrier 430 always knows the next routing step, and optionally subsequent routing steps.

In this example, carrier 430 receives a route list representing Route 2 from central management processor 440 instructing it to proceed via section G to decision point 412. At decision point 412, carrier 430 will initiate switching onto section A by interacting with a gate or by turning as described above. Carrier 430 can take into account curved track conditions on section G and section A to ensure that acceleration and jerk conditions do not exceed a threshold requirement for the sample it carries. This can prevent spillage or instability during transit. The route information received by carrier 430 then instructs carrier 430 to proceed through decision point 402 without turning. The trajectory used in Route 2 when approaching decision point 402 can be different (e.g., faster) from that used during Route 1, because carrier 430 knows that it does not need to make a sharp right turn onto section G. In some embodiments, this allows carrier 430 to approach decision point 402 with a substantially greater velocity during Route 2 than during Route 1. By traversing decision point 402 faster if carrier 430 is not turning, carrier 430 can complete Route 2 in less time than embodiments in which carrier 430 must slow down for possible switching at each decision point. This is an improvement over the prior art, where carriers are typically halted and singulated, regardless of whether the carrier is turning or not.

After passing decision point 402, carrier 430 proceeds onto section B. At decision point 404, carrier 430 proceeds to section C. At decision point 406, carrier 430 prepares and turns onto section I, where it stops for interaction with pipette 424. Like section G, section I can act as a queue for pipette 424 and carrier 430 can be controlled under local instruction by the analyzer/testing station 205B served by section I.

When pipette 424 is done interacting with carrier 430, central management processor 440 can provide new routing instructions to carrier 430 instructing carrier 430 to proceed onto an output path K. Route 3 can be handled in the same manner as Route 1 and Route 2. Upon receiving instructions for Route 3, carrier 430 proceeds down section I to decision point 408 where it turns back onto a main track section E and proceeds past decision point 410, track section F, and decision point 412 (without needing to slow down in some embodiments), and onto section K where the carrier 430 and/or the sample can be removed from the system by an operator. Carrier 430 can then be reused for samples at input section J. Upon receiving instructions for Route 4, carrier 430 proceeds down section D to sample handling station 205C and to decision point 408 where it turns back onto a main track section E and then proceeds the same as Route 3.

FIG. 7 shows a general operational diagram of carrier 430 as it follows routing instructions. As can be seen in method 450, the actions can be taken by the carrier with minimal control by, or interaction with, a central scheduler, such as a central management controller. At step 451 the carrier receives routing instructions from, for example, a central scheduler. In this example, the routing instructions include enough information for the carrier to determine its entire route to a destination point in the track system. These instructions can include a list of all routing points, including decision points to turn at and sections to traverse. In some embodiments, routing instructions can include the destination point and onboard routing information can be used by the carrier to determine the best route to take. It will be appreciated that, when at least a main track is unidirectional, the routing calculation by the carrier is fairly simple and can comprise any known method including searching a tree of nodes and sections or searching a lookup table of possible route permutations.

These instructions can also include velocity and acceleration motion profiles for each section. In some embodiments, velocity and acceleration for each section of track can be calculated by the carrier based on its payload and based on information in an onboard database, such as length of track, curvature of track, location of decision points, the type of sample or payload being carried, and consideration of whether the carrier will turn or proceed in the same direction upon reaching a decision point. In some embodiments, the routing information received at step 451 also includes timing information to instruct the carrier when to begin transit and/or when to complete transit.

Upon receiving routing instructions and beginning transit, the carrier determines its current location and optionally the direction needed to begin its route at step 452. In a general sense, a carrier can only move in two directions, forward or backwards and, in some embodiments, initiate a turn while moving. Because of the simplified movement model, a carrier can begin its transit even if it only has a rough understanding of its current location, such as by acquiring the current track section by RFID information. In some embodiments, the carrier uses more precise encoding in the track to determine its current location within a track section before proceeding.

Once the current position and necessary direction is determined, the carrier can begin transit at step 454. By using an understanding of the location on the track, geometry of the current track, distance to the next decision point, type of sample/payload, and current velocity, the carrier can determine a safe acceleration profile to begin transit. For example, if a carrier is a large distance away from the next decision point and is currently stopped, the carrier can begin accelerating at a maximum acceleration for the sample. In some embodiments, the acceleration of the carrier is ramped up to avoid exposing the sample to a high degree jerk.

FIG. 8 shows an exemplary acceleration motion profile that can be used to limit jerk and acceleration, while minimizing transit time. By using a trapezoidal acceleration profile, acceleration is ramped up to avoid unnecessary jerk until acceleration reaches a safe amount that is less than a threshold amount to avoid damaging or spilling the sample. By ensuring that acceleration is less than a threshold amount, a carrier may have some acceleration available to mitigate collisions or handle other unexpected situations without exceeding an acceleration threshold for the payload. Generally, maximum velocity will be reached midway between a start point and a stop point. In some embodiments, there is no top speed for a straight section of track, but curved sections of track are governed by a top speed to prevent excessive lateral acceleration. These speed limits and acceleration thresholds may be known to an intelligent carrier, and may be accessible in onboard memory. The exact motion profile used by a carrier can vary depending on the payload being carried. For example, empty carriers or carriers transporting reagents or non-sample payloads may utilize a motion profile that has higher limits than a motion profile that carries a sample.

Unlike traditional friction tracks, which are governed by a fixed velocity of the track, some embodiments of the present invention can enable dynamic acceleration profiles and allow carriers to move at much greater average velocity than the prior art. In some embodiments, it is generally desirable to limit the maximum transit time between any points within the track system to less than a portion of an operation cycle of the clinical analyzer. For example, if the maximum distance between any points on a track system is 25 m and the operation cycle time is 20 seconds, it may be desirable to ensure that the average velocity of the carrier, including all turns, acceleration, deceleration, starting, and stopping, is sufficient to traverse 30 m in 5 seconds or less, or 6 m/s (~2.1 km/hr). Because a majority of the time in transit is spent accelerating or decelerating, it will be appreciated that the maximum velocity of the carrier on a straightaway can be substantially higher than this average velocity.

Because jerk and acceleration should be limited for samples, real-time control of acceleration is desired. This goal is furthered by giving control of acceleration to the carrier itself so that it can monitor its current trajectory using accelerometers or other sensors. The carrier can dynamically change its trajectory based on track conditions such as location, traffic, and the need to slow down for an upcoming turn. In this manner, the carrier can be responsible for monitoring and controlling its own dynamic stability conditions.

Referring back to FIG. 7, at step 460, the carrier determines whether or not it is safe to continue accelerating or decelerating in accordance with the trajectory determined in step 454. Step 460 can include collision detection or checking for other unexpected obstructions or a system-wide or carrier-specific halt command. In some embodiments, the decision at step 460 is based on collision detection sensors, including RF rangefinders, but can also include status information about the track received from the central management controller or from other carriers at step 455. This status information can include, for example, position and trajectory information about surrounding carriers or updated commands such as a halt instruction or new route instructions.

If the carrier determines at step 460 that it is not safe to continue with the planned trajectory, the carrier can take steps to mitigate or avoid a collision at step 462. For example, if it is determined that the acceleration profile will place the carrier dangerously close to another carrier, the carrier can begin slowing down. In some embodiments, the decision to slow down to avoid collision is based on an extrapolation of the current trajectory and the observed trajectory of the other carrier. If it is determined that the current trajectory will cause the carrier to come within an unsafe following distance from the carrier ahead of it, the mitigation procedure will be initiated. In some embodiments, each carrier is modeled as having a collision zone into which it is unsafe to enter. This collision zone moves with the carrier. If a carrier senses that it will invade a collision zone of another carrier (or another carrier will invade the instant carrier's collision zone), the carrier can mitigate the collision by decelerating (or accelerating to avoid a rear end collision in some embodiments).

After the carrier decelerates/accelerates to mitigate a collision, the carrier proceeds back to step 454 to determine an updated trajectory that takes into account the new collision avoidance conditions. If no unsafe condition is detected, the carrier proceeds with implementing its trajectory at step 464 (e.g., proceed with a portion of the trajectory before repeating steps 454-460 to allow for continuous monitoring of conditions). This can include accelerating or decelerating and observing track encoding and accelerometer information to determine its current status and trajectory. In some embodiments, the carrier will communicate its current status, including location, trajectory, and/or planned trajectory to the central controller and/or other carriers to assist in routing and collision avoidance at step 465.

As the carrier begins iteratively implementing its planned trajectory, it observes the track for upcoming landmarks, such as its terminal destination or an upcoming decision point at step 470. These landmarks can be identified via important features in the track, such as a warning or braking LED, by extrapolating the distance to a landmark from the observed encoding, or by some combination thereof. If no landmark is upcoming, the carrier continues to step 454 and continues iteratively calculating and implementing a planned trajectory.

In this example, there are two types of important landmarks. The first landmark is the destination of the carrier. The carrier can determine if it is nearing its destination based on track encoding or a landmark feature such as an LED and uses information to begin stopping or complete a stopping procedure at step 472. For example, a carrier may be instructed to stop at a precise location accessible to a pipette. This precise location may include an LED in the wall or floor of the track to assist a carrier in the stopping at a precise location with millimeter accuracy. In some embodiments, the calculated trajectory at step 454 is used to get a carrier in a rough location of its destination, while a stopping procedure at step 472 is used to determine the precise stopped location, such as by searching for a nearby LED landmark and stopping at the appropriate position.

Another important landmark is a decision point. Encoding or warning LEDs in the track can convey the position of an upcoming decision point to a carrier. For example, a central management controller may illuminate an LED at a braking position on the track some distance before a decision point to alert the carrier to decelerate to prevent unnecessary acceleration or collision at decision point. In other embodiments, the carrier extrapolates the relative position of an upcoming decision point from the track encoding and uses this distance to update its trajectory, if necessary, at step 474. At step 474, a carrier determines the relative location of a decision point and determines, based on its routing information, if the carrier will be turning or proceeding at the decision point. If the carrier will be turning, it may be necessary to update the trajectory to begin decelerating so that the velocity of the carrier is slow enough when it turns at the decision point to prevent unnecessary lateral forces that could harm or spill a sample.

In many instances, the carrier will be proceeding past the decision point without turning. In these instances, it may not be necessary to update the trajectory and the carrier can continue at its current velocity or even continue to accelerate through the decision point.

If the carrier determines that it needs to turn at the upcoming decision point, the carrier can slow down and initiate the turn at step 476. In some embodiments, the carrier is only capable of forward or backwards movement without assistance. In these embodiments, the carrier or central management controller can communicate with a switching mechanism at the decision point, at step 477, to ensure that any mechanical or electromagnetic devices in the track system 400 are engaged to direct the carrier in the appropriate direction when it traverses the decision point. Examples of devices in the track can include mechanical switches that block one path at a fork and assist the carrier in turning down the other path at the fork (like a railroad switch that can be mounted to rails or a gate when the track is shaped like a trough), magnets that pull the carrier in one direction or another, or changing signaling in the path that assists the carrier in turning, such as an LED that the carrier follows or an LCD or e-ink panel in the track that includes a line that can be followed by the carrier if the carrier is equipped with traditional line-following capabilities. Unlike prior art configurations that may singulate, scan, and push individual carriers after they stop at a decision point, some embodiments of the present invention can negotiate a turn before a carrier physically arrives at a decision point. This can allow a carrier to proceed at a velocity limited by the curvature of a turn, rather than having to stop or wait for other mechanisms in order to turn.

In embodiments where a carrier has some steering capability and can turn at a decision point without the assistance of the next internal switch, the carrier can engage its steering mechanism to direct it to the appropriate path upon approaching the decision point. After turning at the decision point (or proceeding without turning) a carrier returns to step 454 to determine its next trajectory.

Although the invention has been described with reference to exemplary embodiments, it is not limited thereto. Those skilled in the art will appreciate that numerous changes and modifications may be made to the preferred embodiments of the invention and that such changes and modifications may be made without departing from the true spirit of the invention. It is therefore intended that the appended claims be construed to cover all such equivalent variations as fall within the true spirit and scope of the invention.

The systems discussed herein can be managed by any suitable means, including one or more processors (e.g., a CPU, DSP, APU, GPU, single or multi-core processors, etc. along with suitable memory and hardware) that may be local and dedicated to a module, shared by modules, part of a larger central controller system, or remote processors available via a network. The means could additionally, or alternatively, include dedicated circuits (e.g., ASICs, FPGAs, etc.) or other hardware suitable for creating an electrical output from sensor input. The processors or circuits can receive input about samples/payload and/or sample carriers in the queue from memory and/or sensors to determine any status information about a queue. These processors or circuits can direct the samples and carriers holding the samples via any suitable means, including electrical/mechanical mechanisms of the automation system or local module that operates under the control of, or in response to, the processors or circuits. It should be understood that the term processor could encompass single or multiple processors which may operate together or separately, and can include general purpose computers operating on a network or standing alone. In some embodiments, the electrical/mechanical mechanisms operate independently of the processors or circuits handling the queues, but the processors or circuits can send requests for motion via any suitable protocol, such as a wireless protocol, such as XBee, wired protocol, such as CAN, or other suitable means. The mechanism used to move samples and their carriers can be in any suitable form, including magnetic motion, linear motors, gears, friction surfaces, air, or pneumatic, hydraulic, or electromagnetic mechanisms. In some embodiments, the motive force is generated by the automation system, the local analyzer module, the sample carriers, or any combination thereof.

In embodiments where a carrier has some steering capability and can turn at a decision point without the assistance of the next internal switch, the carrier can engage its steering mechanism to direct it to the appropriate path upon approaching the decision point. After turning at the decision point (or proceeding without turning) a carrier returns to step 504 to determine its next trajectory.

Multiple Slot Carrier

In some conventional systems, a substantial amount of time for each carrier may be spent waiting in sample handling queues at sample handling stations because of the time required for a place and pick device to perform discrete place and pick operations by transporting a picked sample from a carrier to storage (pick operation) and placing a retrieved sample from storage onto the carrier (place operation). For example, when multiple carriers queue up at a sample handling queue, the place and pick device picks a sample from the first carrier and transports the sample from the first carrier to storage. The place and pick device then retrieves a sample from storage and places the retrieved sample onto the first carrier. The first carrier and any additional carriers in the queue behind the first carrier, however, must wait in the queue during the time required for the place and pick device to transport the picked sample from the first carrier to storage and place the retrieved sample from storage onto the first carrier. This cycle repeats as the place and pick device picks a sample from the next carrier and transports the picked sample from the next carrier to storage and places a new sample from storage onto the next carrier. During each repetition, one or more carriers wait in the queue after the sample is picked until the place and pick device returns from storage and places a new sample retrieved from storage onto the next carrier.

The wait time in the queue increases the latency experienced by each sample and the IVD system overall. Certain types of samples, such as whole blood samples, can begin to separate or coagulate if the sample sits in the sample tube for too long. Further, the entire queue may need to be flushed to make way for a STAT sample that an operator wishes to have moved to the front of the line so that results for that sample can be returned quickly, increasing the overall latency experienced by non-STAT samples.

In some conventional systems, carriers of one sample queue must wait for the place and pick device in another sample queue to return from storage and place a new sample retrieved from storage onto the next carrier. Further, sample handling queues may be on a track shared with other carriers. These other carriers may or may not require sample handling (e.g. place and pick operations) at each queue.

In some of these conventional multiple queue systems, pullouts or side cars, such as for example, the pullouts 112, 122, 132 shown at FIG. 1 are included to prevent queues from clogging main tracks. Some embodiments of the present invention eliminate the need for side cars, reducing costs and complexity. Other embodiments of the present invention may, however, be used with side cars to improve the efficiency and reduce the latency incurred at the sample handling queues.

Place and pick devices may also perform combined place and pick operations by placing a sample in a sample carrier and picking a sample from a sample carrier without having to travel to and from a sample storage area. In some conventional systems, combined place and pick operations may be performed on two separate single slot sample carriers. In these single slot sample carrier systems, however, a queue of at least two sample carriers is required to perform combined place and pick operations.

Embodiments of the present invention may utilize multiple slot carriers and one or more algorithms where each multiple slot sample carrier has at least one empty slot at a place and pick device for performing a combined place and pick operation on a single multiple slot sample carrier, thereby reducing or eliminate sample handling queues experienced by carriers at place and pick devices, without the need for side cars, by performing combined place and pick operations using multiple slot carriers.

Embodiments of the invention include improved systems and methods for decreasing carrier wait times at sample handling stations by including carriers having a plurality of slots, each being configured to hold a fluid container (e.g. a sample). For example, as shown at FIG. 9A to FIG. 9D, a carrier 500 may include a carrier body 502 and a plurality of slots 504 and 506. Slots 504 and 506 may be configured to hold a fluid container, such as fluid containers (e.g. sample tubes) 508 and 510. Each fluid container 508 and 510 is configured to hold one or more fluids. The size and shape of the carrier and fluid container in the embodiment shown at FIG. 9A to FIG. 9D is exemplary. Embodiments may include carriers and/or fluid containers having other sizes and shapes.

In some embodiments, an automation track system, such as the system 400 shown at FIG. 6, may include a plurality of multiple slot carriers, such as carrier 500. As described above, carrier 430 in system 400 can be any suitable embodiment of a carrier, such as multiple slot carrier 500, shown at FIG. 9A to FIG. 9D. System 400 may also include place and pick device 426 at sample handling station 205C. When multiple slot carriers, such as carrier 430, enter a queue at sample handling station 205C, place and pick device 426 may be configured to place fluid containers, such as fluid containers 508, 510 into slots 504, 506 and/or remove the fluid containers 508, 510 from the slots 504, 506.

Embodiments of the invention may include any place and pick device configured to pick up objects, move the objects to and from different areas and place the objects somewhere. Place and pick devices may include robotic arms having one or more movable joints capable of moving in one or more dimensions, slidable portions moving in one or more dimensions, and a variety of types of actuation devices for moving one or more portions of the pick and place devices, such as linear actuators, pneumatic actuators, hydraulic actuators and electro-mechanical actuators.

System 400 may also include a storage area 428 accessible to the place and pick device 426 and configured to hold fluid containers 508 and 510. Controller 440 may be configured to control the place and pick device 426 to perform place and pick operations and maintain at least one empty slot on the carriers between place and pick operations, for example, as described in more detail below with reference to the flow diagram at FIG. 11.

Figure 9B:
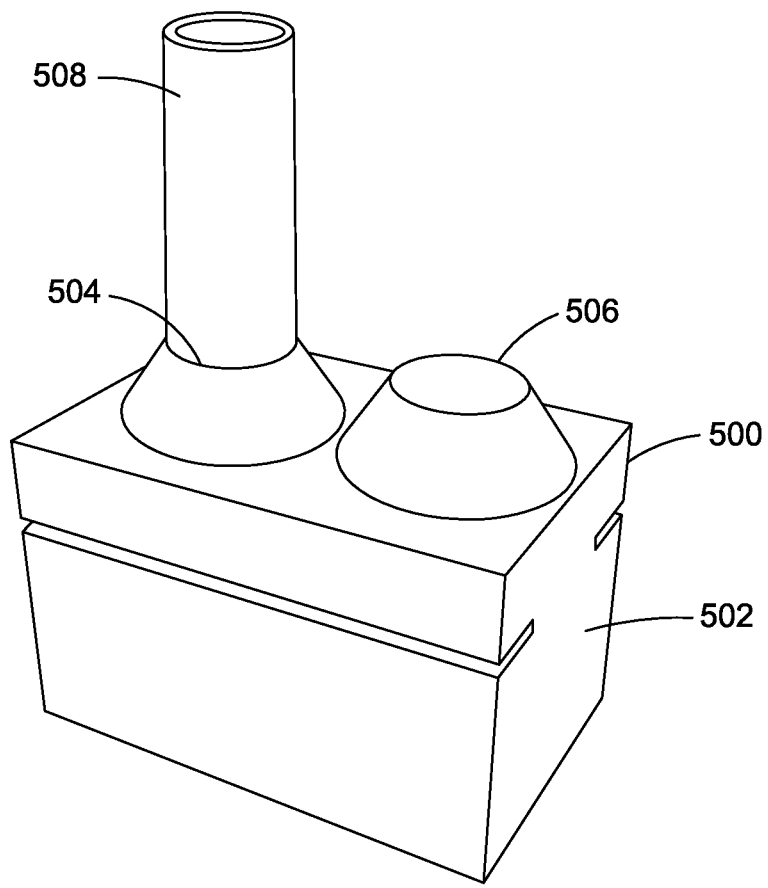
FIG. 9B to FIG. 9D are perspective views of an exemplary carrier having two slots at different states of a place and pick operation that can be used with the embodiments disclosed herein.

In some embodiments, a system, such as system 400, may include one or more sensors configured to sense the presence or absence of fluid carriers in the carriers' slots. For example, one or more sensors may sense that slot 506 of carrier 500 is empty and/or that slot 504 of carrier 500 is occupied by fluid container 508, as shown at FIG. 9B. In some embodiments, a multiple slot carrier, such as carrier 500, may include the one or more sensors, such as sensor 317 shown at FIG. 5, to sense the presence or absence of fluid containers 508, 510 in slots 505, 506. For example, sensors may include a mechanical switch that is depressed by the presence of a container and not depressed when a container is absent. Sensors, such as sensor 317, may also include an optical or capacitive sensor to sense the presence or absence of fluid containers.

In some embodiments, the one or more sensors may be external to the carriers. The one or more sensors may be positioned at one or more locations around the system to determine the presence or absence of fluid containers in carrier slots. For example, the place and pick device 426 may include the one or more sensors and may be optically configured to observe a carrier via an image or an IR beam. Optionally, a controller, such as controller 440 may record the presence or absence of fluid containers in carrier slots and later direct a carrier to one or more locations for place and pick operations.

In some embodiments, the multiple slot carriers may include onboard processors, such as onboard processor 301 shown at FIG. 5. Multiple slot carriers, such as carrier 430, shown at FIG. 6, and carrier 500, shown at FIG. 9A through FIG. 9B, may include a transceiver in communication system 315, shown at FIG. 5, to communicate with the onboard processor 301 and the controller 440, shown at FIG. 6. Multiple slot carriers 430, 500 may be instructed by controller 440, via communications system 315, to perform general operations of traveling along different routes and to stations along a track, while onboard processor 301 may implement more specific operations, such as for example, directing the multiple slot carrier 430, 500 to one or more locations at a sample handling station, for having a first fluid container 510 placed into empty slot 506 and having a second fluid container 508 subsequently removed or picked from occupied slot 504 (see e.g. FIGS. 9B-9D).

In some embodiments, the multiple slot carriers 430, 500 may be instructed by controller 440, via communications system 315, to perform the general operations described above and the more specific operations, while the onboard processor 301 merely executes the instructions from the controller 440. In some embodiments, one or more controllers may cause the track to direct the carriers 430, 500 to stations along the track and to the one or more locations at a sample handling station 205C for the place and pick operations.

Figure 10A:
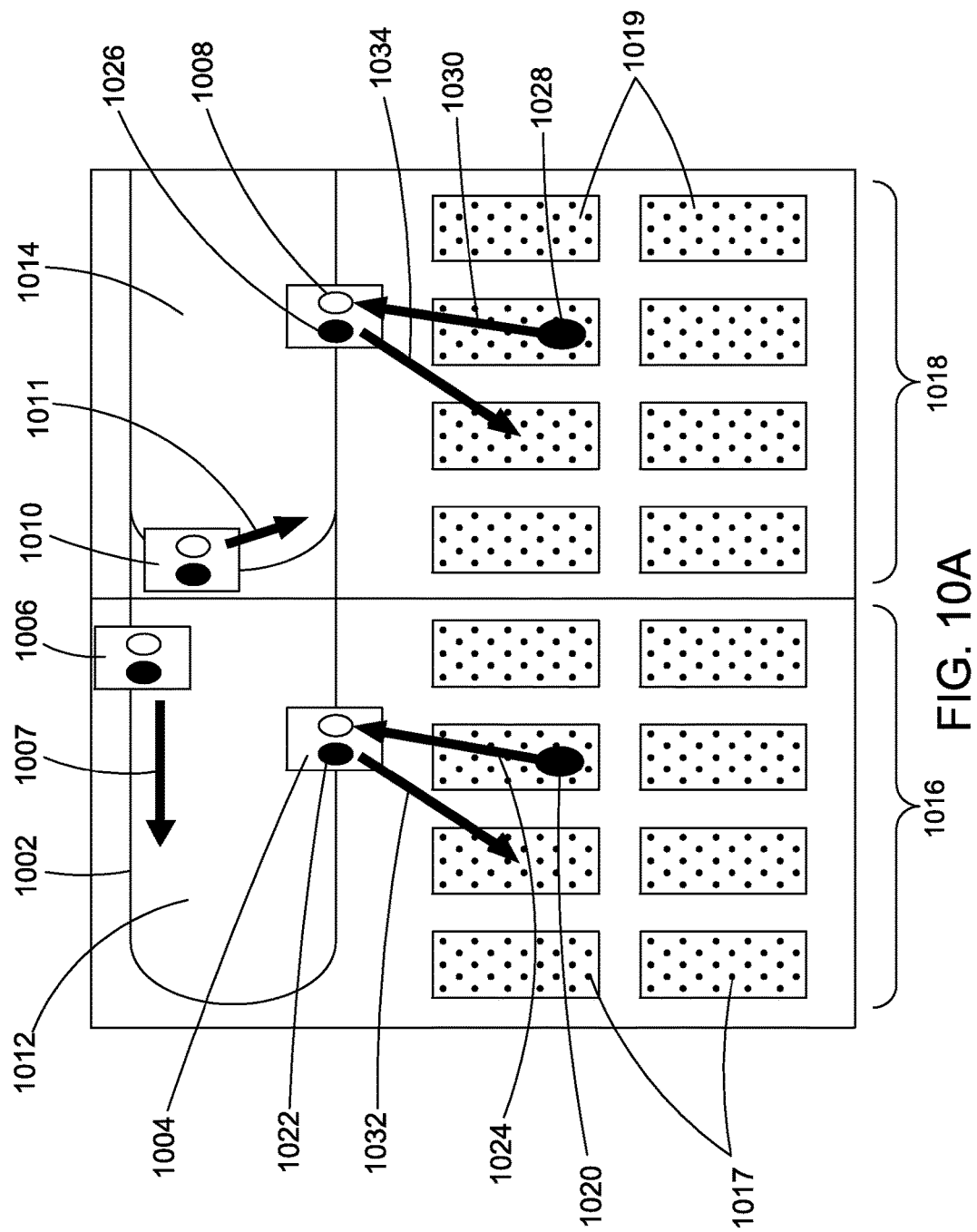
FIG. 10A and FIG. 10B are schematic diagrams illustrating a plurality of multiple slot carriers along a track having first and second sample handling queues during different states of place and pick operations that can be used with the embodiments disclosed herein.
Figure 10B:
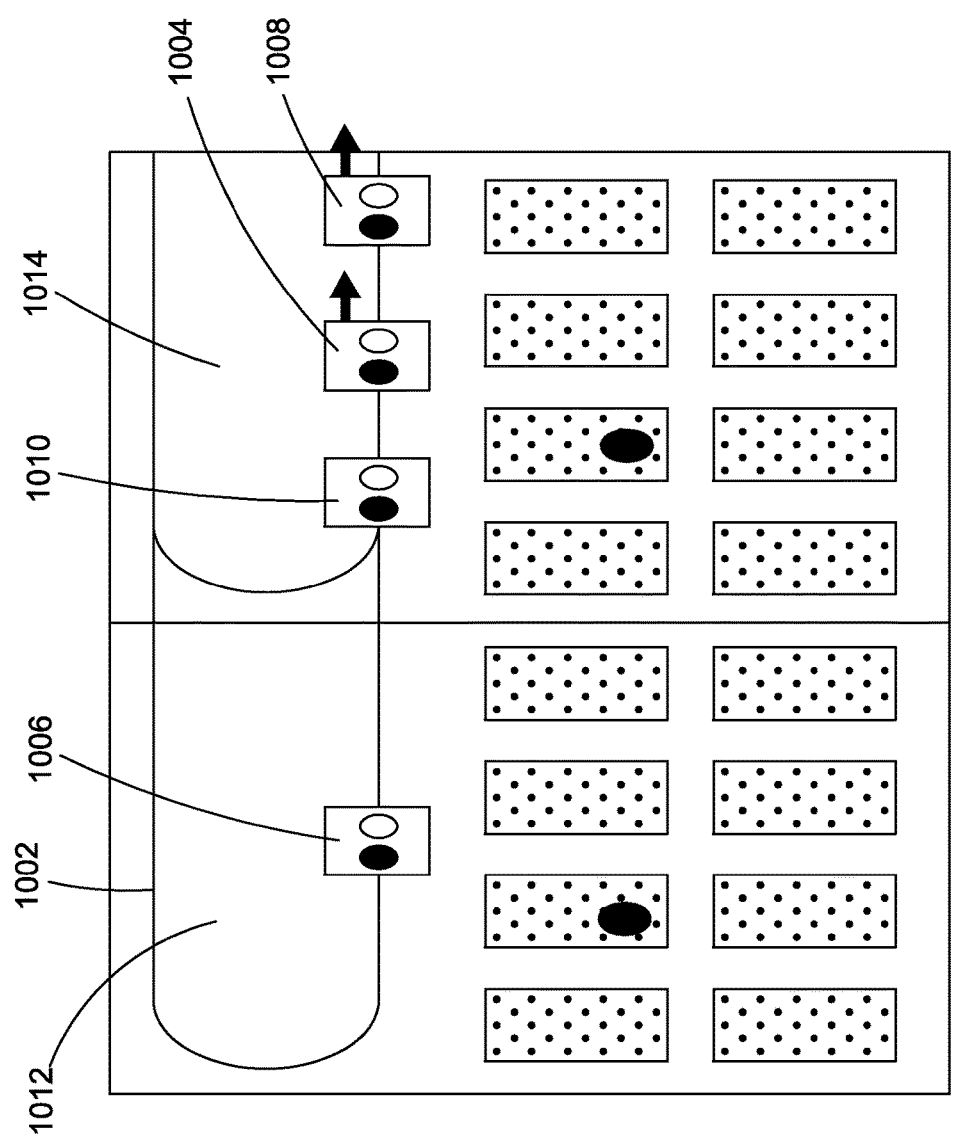
Figure 11:
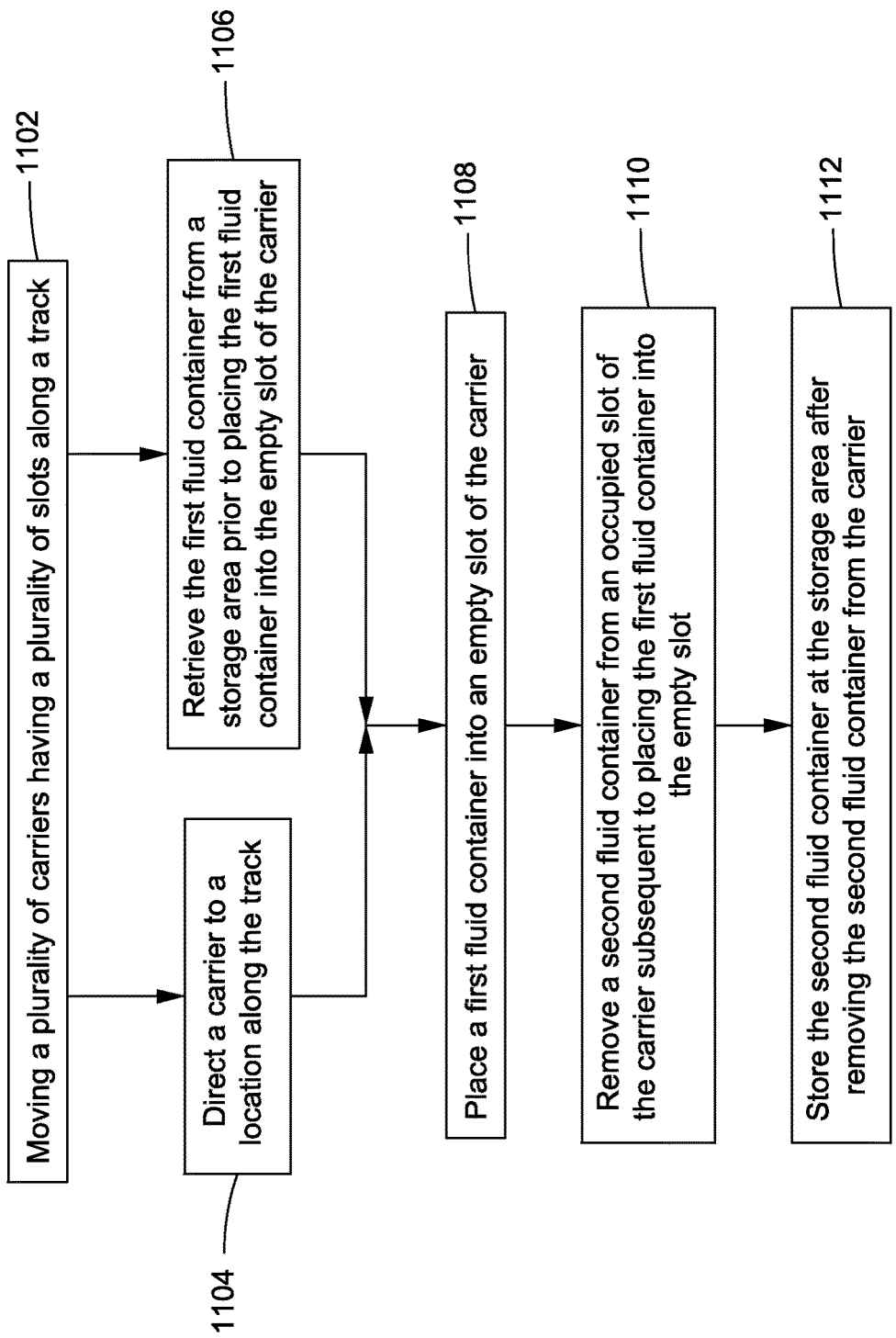
FIG. 11 is a flow diagram illustrating a method for operating an in-vitro diagnostics system that can be used with the embodiments disclosed herein.

FIG. 10A and FIG. 10B are schematic diagrams illustrating a plurality of multiple slot carriers along a track having first and second sample handling queues during different states of place and pick operations. FIG. 11 is a flow diagram illustrating a method for operating an in-vitro diagnostics system that can be used with the embodiments disclosed herein. The flow diagram at FIG. 11 will now be described with reference to the multiple slot carriers during different states of place and pick operations shown at FIG. 10A and FIG. 10B. At block 1102, a plurality of carriers having a plurality of slots may move along a track. For example, as shown at FIG. 10A, track 1002 includes a plurality of carriers 1004, 1006, 1008 and 1010 at different locations along a track 1002. The direction of movement is indicated by arrows 1107 and 1011.

At block 1104 of FIG. 11, a carrier may be directed to a location along the track. For example, as shown at FIG. 10A, carrier 1004 may be directed to a location at a first sample handling queue 1012 while carrier 1006 is being directed to the first sample handling queue 1012 in the direction indicated by arrow 1007. Carrier 1008 has been directed to a location at a second sample handling queue 1014 while carrier 1010 is being directed to the second sample handling queue 1014 in the direction indicated by arrow 1011. Each of the carriers 1004, 1006, 1008 and 1010 may be directed to their respective locations at the first handling queue 1012 and the second handling queue 1014 by onboard processors, such as onboard processor 301 and by one or more controllers, such as controller 440 or by operation of individual magnets in the track.

When each of the carriers 1004, 1006, 1008, 1010 arrive at respective locations at the first handling queue 1012 and the second handling queue 1014, place and pick operations may be performed by a place and pick device, such as place and pick device 426, shown at FIG. 6. The place and pick operations will now be described with reference to FIG. 9A to FIG. 9D, which shows a carrier 500 at different states prior to, during and after the place and pick operations, as well as FIGS. 10A and 10B, which shows a plurality of multiple slot carriers positioned along a track 1002 having first and second sample handling queues 1012 and 1014 during different states of place and pick operations.

As shown at FIG. 10A, carrier 1004 may arrive at a location at first handling queue 1012. At this pre-placing state, carrier 1004 includes fluid container 1022 in an occupied slot and no fluid container in an empty slot. FIG. 10A also shows carrier 1006 approaching first handling queue 1012 while carrier 1004 is at its location at first handling queue 1012 during the pre-placing state. FIG. 10A also shows carrier 1008 at its respective location at second handling queue 1014. At this pre-placing state, carrier 1008 includes fluid container 1026 in an occupied slot (represented by solid dot) and no fluid container in an empty slot (represented by white dot). Controller 440 may maintain one or more slots as empty slots, such as the empty slot on carrier 1004 in between place and pick operations. For example, controller 440 may maintain the empty slot prior to the fluid container 1022 being placed into the empty slot. FIG. 10A also shows carrier 1010 approaching second handling queue 1014 while carrier 1008 is at its location at second handling queue 1014 during the pre-placing state. The embodiment shown at FIG. 9B is a perspective view of a carrier 500 at a pre-placing state. As shown in FIG. 9B, carrier 500 includes fluid container 508 in occupied slot 504 and no fluid container in empty slot 506.

At block 1106 of FIG. 11, a first fluid container may be retrieved from a storage area. In some embodiments, blocks 1104 and 1106 may be occurring simultaneously. That is, a first fluid container, such as container 1020 may be retrieved from a storage area simultaneous with a carrier, such as carrier 1004, being directed to a location along the track. For example, as shown at FIG. 10A, while carrier 1004 is being directed to first handling queue 1012, a controller, such as controller 440 may simultaneously cause a place and pick device, such as device 426, to retrieve fluid container 1020 from storage area 1016, as indicated by arrow 1024. Accordingly, when carrier 1004 arrives at first handling queue 1012, place and pick device 426 is in a position to place the first fluid container 1020 into the empty slot of the carrier 1004. Further, while carrier 1008 is being directed to second handling queue 1014, controller 440 may simultaneously cause a place and pick device, such as device 426, to retrieve fluid container 1028 from storage area 1018, as indicated by arrow 1030. Accordingly, when carrier 1008 arrives at second handling queue 1014, place and pick device 426 is in a position to place fluid container 1028 into the empty slot of the carrier 1008. Because respective pick and place devices are in positions to place fluid containers into empty slots of carriers, less time may be spent by carriers waiting in sample handling cues, thereby reducing clogging along the track.

In some embodiments, each place and pick device may be controlled by a respective sub-controller. In some embodiments, the place and pick devices may be controlled by a central controller, such as controller 440 at FIG. 6. In the embodiment shown at FIGS. 10A and 10B, storage areas 1016 and 1018 include sub-storage areas 1017 and 1019, respectively. Exemplary storage areas may include any number of sub-storage areas. In some embodiments, a storage area may not include any sub-storage areas. Storage areas and sub-storage areas may be of any shape and size adapted to receive and hold fluid containers. Storage areas and sub-storage areas may also include one or more sensors for sensing the presence or absence of a fluid container.

Figure 9C:
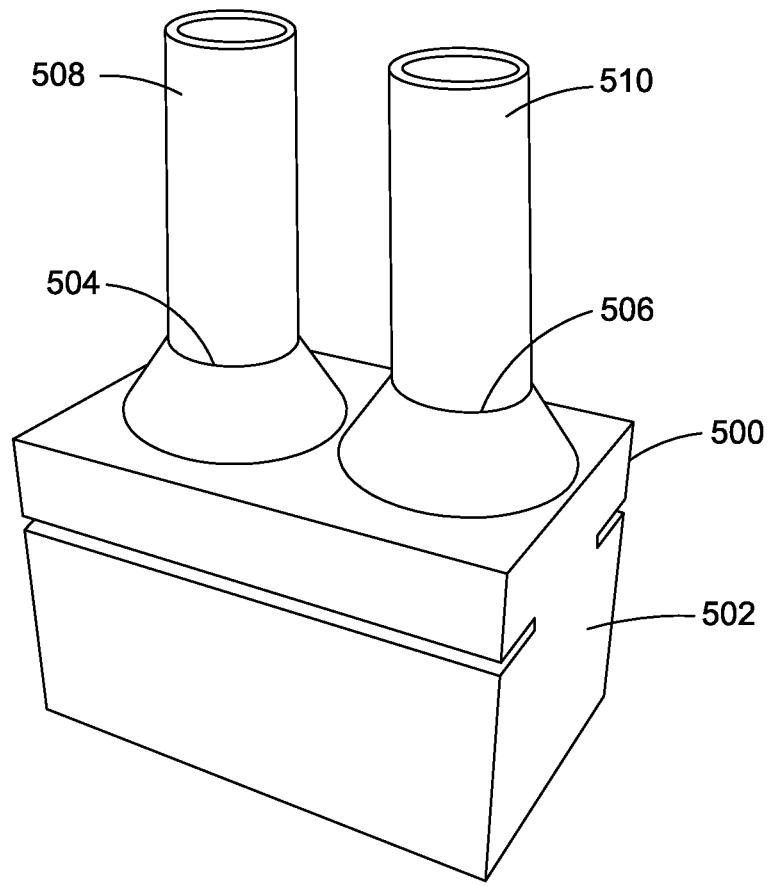

At block 1108 of FIG. 11, the first fluid container may be placed into the empty slot of the carrier using a place and pick device. For example, controller 440 may control the place and pick device 426 to place fluid container 1020 into the empty slot of carrier 1004 while fluid container 1022 is in the occupied slot. FIG. 10A also shows carrier 1008 at its respective location at second handling queue 1014. Controller 440, or a separate sub-controller (not shown), may control another place and pick device, such as device 426, to place fluid container 1028 into the empty slot of carrier 1008 while fluid container 1026 is in the occupied slot. The embodiment shown at FIG. 9C is a perspective view of carrier 500 after a place and pick device, such as device 426, has placed fluid container 510 into previously empty slot 506. As shown, carrier 500 includes fluid container 508 in occupied slot 504 and fluid container 510 in previously empty and now occupied slot 506.

Figure 9D:
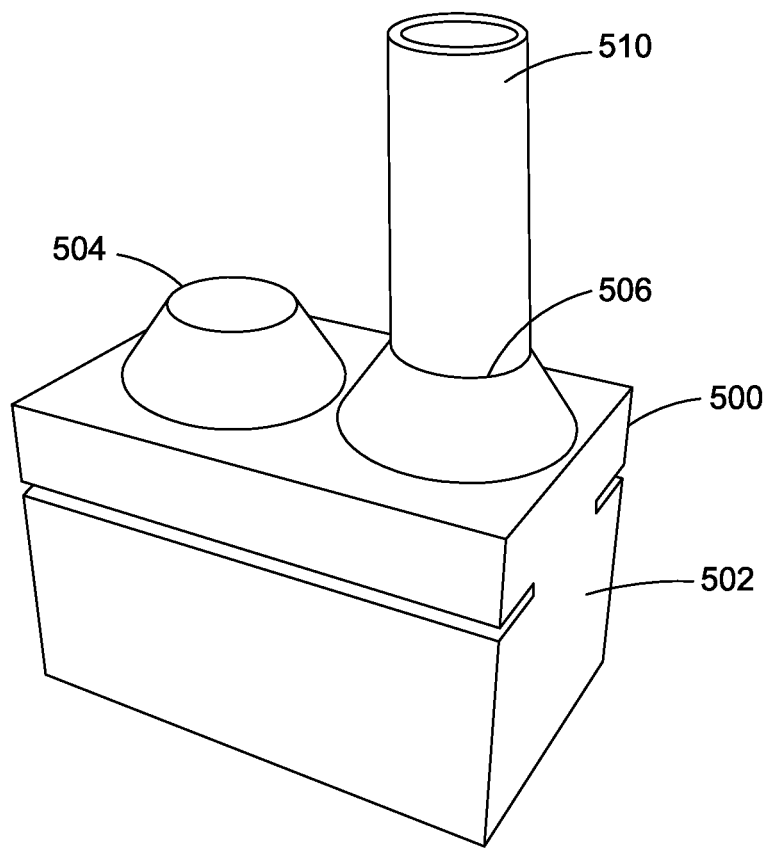

At block 1110 of FIG. 11, the second fluid container may be removed from the occupied slot of the carrier subsequent to placing the first fluid container into the empty slot. For example, after fluid container 1024 has been placed into the previously empty slot, controller 440 may then control the place and pick device 426 to remove fluid container 1022 from the occupied slot of carrier 1004. Controller 440, or a separate sub-controller may also control a place and pick device, such as device 426, to remove fluid container 1026 from the occupied slot of carrier 1008 after fluid container 1028 has been placed into the previously empty slot. The embodiment shown at FIG. 9D is a perspective view of carrier 500 after a place and pick operation has been performed. As shown in FIG. 9D, carrier 500 includes fluid container 510 in previously empty and now occupied slot 506 while previously occupied slot 504 is now empty. As described above, controller 440 may maintain one or more slots on the multi slot carriers as empty in between place and pick operations. For example, controller 440 may maintain previously occupied, and now empty slot 504, as empty until another place and pick device performs a place and pick operation using carrier 500.

In some embodiments, both the placing of the first fluid container into the empty slot and the removing of the second fluid container from the occupied slot may be performed while the carrier is at a single location on the track. That is, the place and pick operations are performed by moving the place and pick device while the carrier remains stationary. For example, place and place device 426 may move to the location of the empty slot 506 and place the first fluid container 510 into the empty slot 506. The place and pick device 426 may then move to the location of the occupied slot 504 and remove the second fluid container 508 from the occupied slot 504. In some embodiments, the place and pick operations are performed by moving the carrier. For example, carrier 500 may be directed to a first location along a track, such as a location at a sample handling queue. While at the first location, the first fluid container 510 may be placed into the empty slot 506. The carrier 500 may then be directed to a second location along the track, such as a second location at the sample handling queue, to remove the second fluid container 508 from the occupied slot 504. Carrier 500 may be directed to the first carrier location and the second carrier location by an onboard processor, such as processor 301, an external central controller, such as controller 440 or a sub-controller (not shown). Place and pick device 426 may be controlled to perform the place and pick operations at the first and second carrier locations.

After the place and pick operations are performed, the second fluid container may be stored at the storage area. For example, referring to FIG. 10A, after fluid container 1022 is removed or picked from carrier 1004, controller 440 may then control the place and pick device for the first sample handling queue 1012 to store fluid container 1022 at storage area 1016, as indicated by arrow 1032. Further, after fluid container 1026 has been removed or picked from carrier 1004, controller 440 may then control the place and pick device for the second sample handling queue 1014 to store fluid container 1026 at storage area 1018, as indicated by arrow 1034.

FIG. 10B shows carriers 1004, 1006, 1008 and 1010 at different states after place and pick operations have been performed on carrier 1004 and carrier 1008. As shown at FIG. 10B, when carrier 1006 arrives at first sample handling queue 1012, carrier 1004 has already exited the first sample handling queue 1012. Accordingly, carrier 1006 does not have to wait in the first sample handling queue 1012 until place and pick operations are performed on other carriers ahead of carrier 1006. Further, when carrier 1010 arrives at second sample handling queue 1014, carrier 1008 has already exited the second sample handling queue 1014. Accordingly, carrier 1010 does not have to wait in the second sample handling queue 1014 until place and pick operations are performed on other carriers ahead of carrier 1010. At their respective states shown at FIG. 10B, carrier 1006 and carrier 1010 are free to undergo place and pick operations. Accordingly, the place and pick operations may be repeated for the newly arrived carriers 1006 and 1010 as described above at block 1106, block 1108 and block 1110. Carrier 1006 and carrier 1010 may also proceed, without waiting, past their respective sample handling queues without undergoing place and pick operations.

Figure 12:
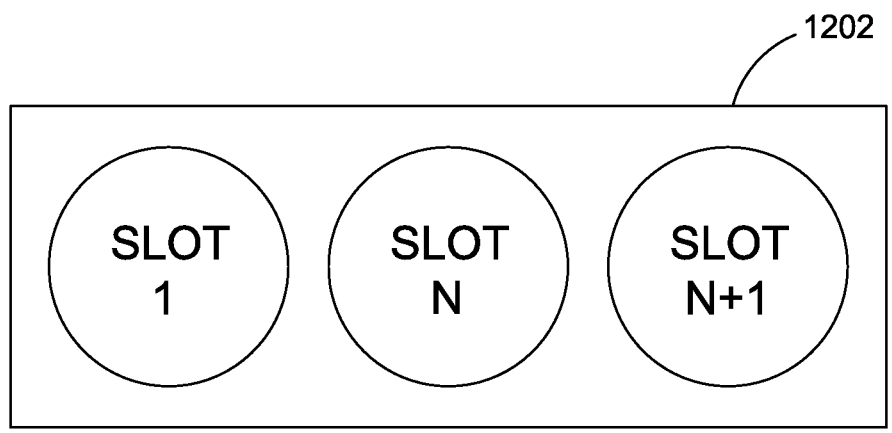
FIG. 12 is a schematic diagram illustrating a carrier having N+1 slots that can be used with the embodiments disclosed herein.

Wait times for newly arriving carriers may be decreased and/or avoided, in part, because an empty slot is maintained on the multiple slot carriers between separate place and pick operations. Therefore, a carrier configured to transport N fluid containers at any one time includes (N+1) slots. FIG. 12 is a schematic diagram illustrating a carrier 1202 having (N+1) slots.

Figure 13A:
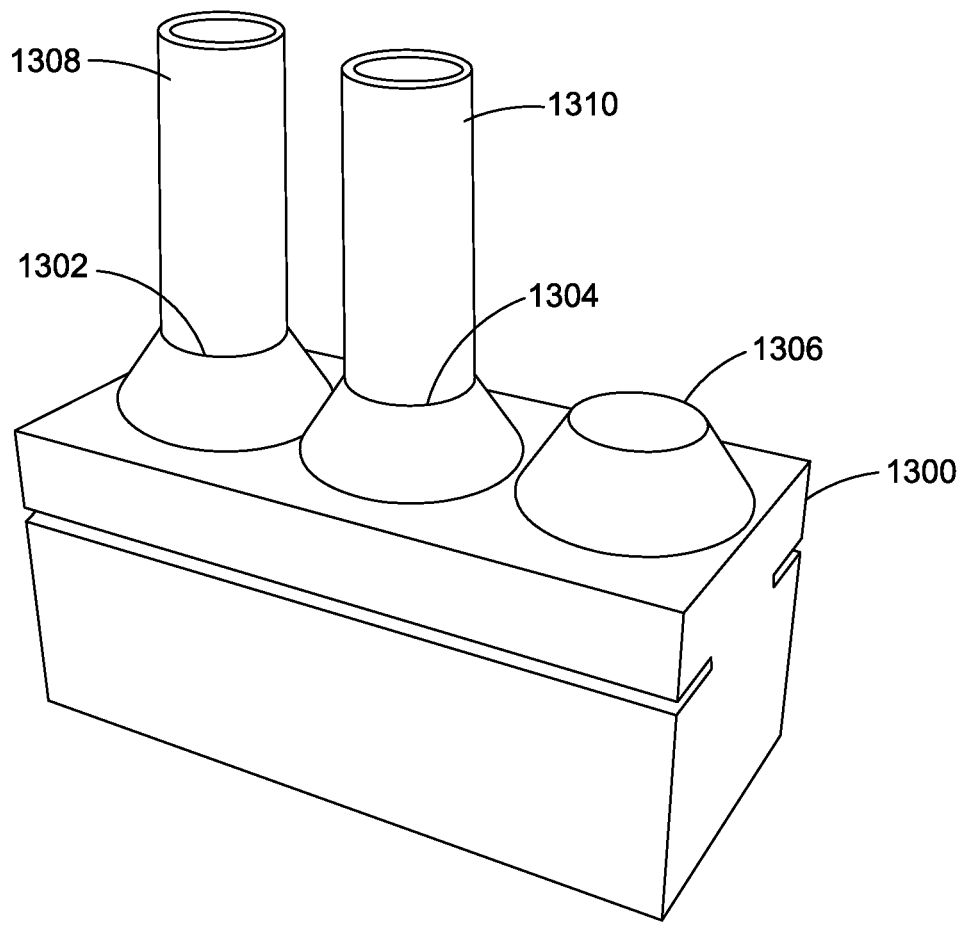
FIG. 13A to FIG. 13C are perspective views of an exemplary carrier having three slots at different states of a place and pick operation that can be used with the embodiments disclosed herein.
Figure 13B:
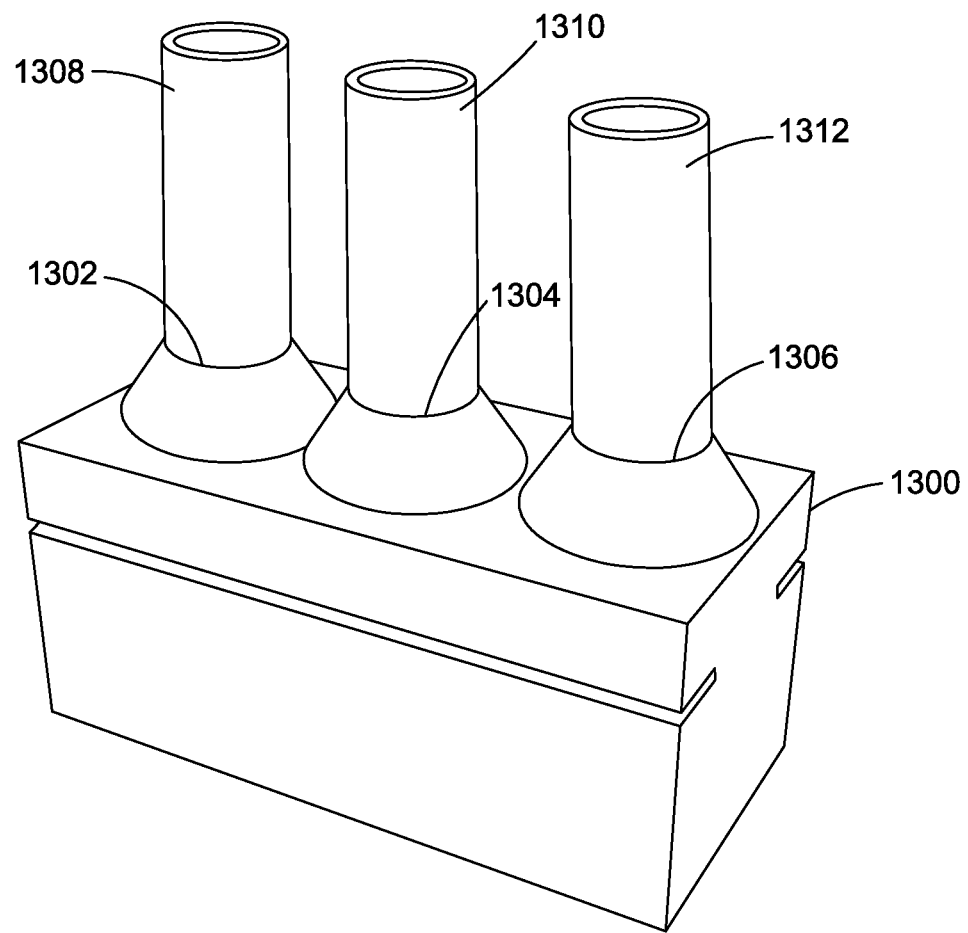
Figure 13C:
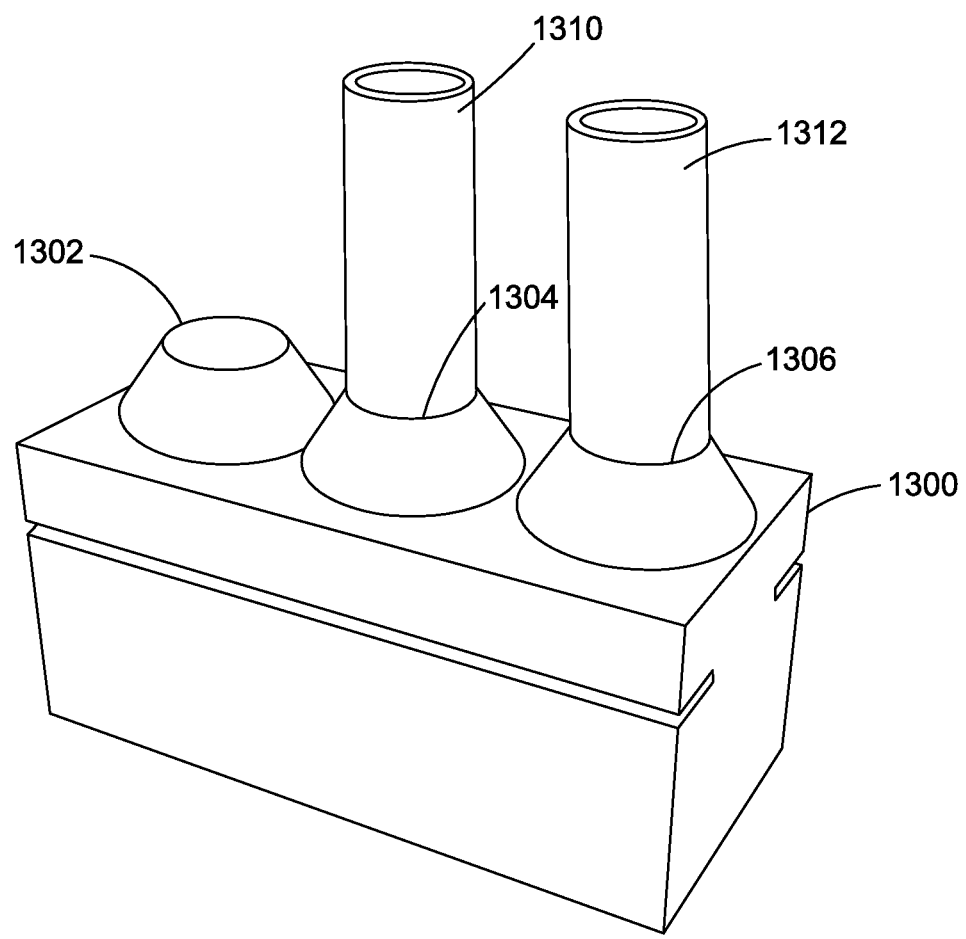

FIG. 13A to FIG. 13C are perspective views of an exemplary carrier 1300 having three slots at different states of a place and pick operation. Carrier 1300 is configured to transport N=2 fluid containers. Accordingly, carrier 1300 includes N+1=3 slots 1302, 1304 and 1306. Therefore, carrier 1300 is configured to maintain an empty slot while simultaneously transporting either 1 or 2 fluid containers along a track between separate place and pick operations. For example, as shown at a pre-placing state in FIG. 13A, slot 1302 and 1304 of carrier 1300 may be occupied by fluid containers 1308 and 1310, respectively, while being directed to a sample handling station, such as sample handling station 205C of FIG. 6. Because slot 1306 is empty, a new fluid container may be placed in empty slot 1306 upon arrival at sample handling station 205C. New fluid container 1312 may then be placed in previously empty and now occupied slot 1306 while slot 1302 and slot 1304 are occupied, as shown at FIG. 13B. Therefore, first slot 1302, second slot 1304 and third slot 1306 are occupied. After fluid container 1312 has been placed into the previously empty slot 1306, fluid container 1308 may be removed or picked from the previously occupied and now empty slot 1302, as shown at FIG. 13C. Accordingly, carrier 1300 maintains an empty slot 1302 for another place and pick operation. Alternatively, rather than fluid container 1308 being picked, fluid container 1310 could have been picked from slot 1304.

In some exemplary embodiments, carriers hold patient sample tubes. It may be appreciated, however, that other embodiments may include carriers that hold any type of payload, such as reagent containers, waste containers or any other objects appropriate to the application.

Although the invention has been described with reference to exemplary embodiments, it is not limited thereto. Those skilled in the art will appreciate that numerous changes and modifications may be made to the preferred embodiments of the invention and that such changes and modifications may be made without departing from the true spirit of the invention. It is therefore intended that the appended claims be construed to cover all such equivalent variations as fall within the true spirit and scope of the invention.

What is claimed is:

1. An automation system for use with in-vitro diagnostics comprising:
   a track configured to provide one or more paths;
   a storage area configured to hold a plurality of fluid containers;
   a plurality of carriers configured to travel along the track, each carrier comprising a plurality of slots, wherein each slot is configured to hold fluid container;
   a place and pick device configured to interact with the plurality of carriers according to steps of:
   (i) retrieving a first fluid container of the plurality of fluid containers from the storage area,
   (ii) placing the first fluid container into an empty slot of the plurality of slots of a carrier of the plurality of carriers before removing any fluid containers from each carrier, (iii) subsequently removing a second fluid container from an occupied one of the plurality of slots of the carrier, and
   (iv) storing the second fluid container in the storage area;
   a controller configured to control the movement of a carrier of the plurality of carriers, such that the carrier travels to the place and pick device with at least one empty slot and to direct the interaction between the place and pick device and the plurality of carriers; and one or more sensors configured to sense which of the plurality of slots of each carrier is empty and which of the plurality of slots is occupied, wherein the controller uses this information to direct the interaction between the place and pick device and the plurality of carriers.

2. The automation system of claim 1, wherein at least one carrier of the plurality of carriers comprises the one or more sensors.

3. The automation system of claim 1, wherein the one or more sensors is configured to observe at least one carrier of the plurality of carriers.

4. The automation system of claim 1, wherein the controller is configured to direct at least one of the plurality of carriers to: (i) a first carrier location for having the first fluid container placed into the empty slot; and (ii) a second carrier location for having the second fluid container subsequently removed from the occupied slot.

5. The automation system of claim 1, wherein at least one carrier of the plurality of carriers comprises an onboard processor.

6. The automation system of claim 5, wherein the at least one carrier further comprises a transceiver configured to communicate with the onboard processor and the controller.

7. The automation system of claim 1, wherein the plurality of slots further comprises at least three slots.

8. The automation system of claim 1, further comprising:
a plurality of electromagnetic coils in at least one of the track and the plurality of carriers; and
a plurality of magnets in at least one of the other of the track and the plurality of carriers,
wherein the plurality of electromagnetic coils and the plurality of magnets are configured to propel the plurality of carriers along the track.

9. A system for transporting fluids in an in-vitro diagnostics environment comprising:
a carrier having:
a carrier body,
at least two slots, wherein each slot is configured to hold one of a plurality of fluid containers, each configured to hold one or more fluids, and
one or more sensors configured to sense which of the plurality of slots of each carrier is empty and which of the plurality of slots is occupied; and
a place and pick device configured to interact with the carrier according to processor controlled steps of:
(i) retrieving a first fluid container from a storage area,
(ii) placing the first fluid container into an empty slot of the carrier before removing any fluid containers from the carrier,
(iii) subsequently removing a second fluid container from an occupied slot of the carrier, and
(iv) storing the second fluid container in the storage area.

10. The carrier of claim 9, further comprising an onboard processor.

11. The carrier of claim 10, wherein the onboard processor is configured to direct the carrier to: (i) a first carrier location for having a first fluid container placed into an empty slot; and (ii) a second carrier location for having a second fluid container subsequently removed from an occupied slot.

12. The carrier of claim 9, further comprising a communications system configured to receive routing instructions, including: (i) a first carrier location for having a first fluid container placed into an empty slot; and (ii) a second carrier location for having a second fluid container subsequently removed from an occupied slot.

13. The carrier of claim 9, wherein the at least two slots further comprises at least three slots.

14. The carrier of claim 9, wherein the carrier is configured to be propelled along a track via magnetic forces.

15. A method for operating an in-vitro diagnostics system, comprising:
moving a plurality of carriers having a plurality of slots and configured to travel along a track;
directing a carrier of the plurality of carriers to a location along the track, wherein the carrier arrives at the location with an unoccupied slot;
sensing which of the plurality of slots of each carrier is occupied;
retrieving a first fluid container of the plurality of fluid containers from the storage area, using a place and pick device,
placing the first fluid container, using the place and pick device, into an empty slot of the carrier at the location, before removing any fluid containers from the carrier, while a second fluid container is in an occupied slot;
removing the second fluid container, using the place and pick device, from the occupied slot of the carrier subsequent to placing the first fluid container into the empty slot; and
storing the second fluid container in the storage area, using the place and pick device, wherein a controller is configured to determine the moving, directing, placing, and removing operations to provide at least one empty slot in the carrier of the plurality of carriers at the place and pick device.

16. The method of claim 15, further comprising directing the carrier to a second location along the track prior to removing the second fluid container from the occupied slot of the carrier.

* * * * *